US011527330B2

(12) United States Patent
Otsuki et al.

(10) Patent No.: US 11,527,330 B2
(45) Date of Patent: Dec. 13, 2022

(54) LEARNING SYSTEM, REHABILITATION SUPPORT SYSTEM, METHOD, PROGRAM, AND TRAINED MODEL

(71) Applicant: Toyota Jidosha Kabushiki Kaisha, Toyota (JP)

(72) Inventors: Nobuhisa Otsuki, Toyota (JP); Issei Nakashima, Toyota (JP); Yoshie Nakanishi, Miyoshi (JP); Manabu Yamamoto, Toyota (JP); Natsuki Yamakami, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 414 days.

(21) Appl. No.: 16/899,948

(22) Filed: Jun. 12, 2020

(65) Prior Publication Data
US 2020/0411195 A1 Dec. 31, 2020

(30) Foreign Application Priority Data
Jun. 27, 2019 (JP) .............................. JP2019-120029

(51) Int. Cl.
*G16H 50/30* (2018.01)
*A61H 3/00* (2006.01)
*G06K 9/62* (2022.01)

(52) U.S. Cl.
CPC ............. *G16H 50/30* (2018.01); *A61H 3/008* (2013.01); *G06K 9/6218* (2013.01); *G06K 9/6256* (2013.01); *A61H 2201/5058* (2013.01)

(58) Field of Classification Search
CPC .. A61H 3/00–068; G06N 3/00–99/007; G06K 9/00–6298; G06V 10/762;
(Continued)

(56) References Cited

U.S. PATENT DOCUMENTS

2015/0294481 A1* 10/2015 Sakaue .................. G06V 40/23
600/595
2015/0342820 A1 12/2015 Shimada et al.
(Continued)

FOREIGN PATENT DOCUMENTS

JP 6052234 B2 12/2016

OTHER PUBLICATIONS

Kim, Jeong Joon, et al. "Personalized recommendation system for efficient integrated cognitive rehabilitation training based on bigdata." International Conference on Human-Computer Interaction. Springer, Cham, 2018. (Year: 2018).*

(Continued)

*Primary Examiner* — Geoffrey E Summers
(74) *Attorney, Agent, or Firm* — Dinsmore & Shohl LLP

(57) ABSTRACT

An acquisition unit acquires a classification result obtained by classifying training assistants by performing a cluster analysis based on first rehabilitation data about rehabilitation performed by the trainee by using the rehabilitation support system, the first rehabilitation data including at least assistant data indicating a training assistant and index data indicating a degree of recovery of the trainee. A learning unit generates a learning model, the learning model being configured to input second rehabilitation data including at least the action data indicating an assisting action performed by the training assistant to assist the trainee and output the action data for suggesting a next action to be performed by the training assistant. The learning unit generates the learning model by using, as teacher data, the second rehabilitation data for which pre-processing has been performed based on the classification result.

20 Claims, 11 Drawing Sheets

(58) Field of Classification Search
CPC .......... G06V 30/19107; G06V 10/774; G06V 30/19147; G06V 10/764; G06V 30/19173
See application file for complete search history.

(56) References Cited

U.S. PATENT DOCUMENTS

2017/0329933 A1* 11/2017 Brust ................ G06F 16/24575
2019/0009133 A1* 1/2019 Mettler May .......... G09B 19/00

OTHER PUBLICATIONS

Mahmoud, Rehab, et al. "Similarity measures based recommender system for rehabilitation of people with disabilities." The 1st International Conference on Advanced Intelligent System and Informatics (AISI2015), Nov. 28-30, 2015, Beni Suef, Egypt. Springer, Cham, 2016. (Year: 2016).*

Ottenbacher, Kenneth J., James E. Graham, and Steve R. Fisher. "Data Science in Physical Medicine and Rehabilitation: Opportunities and Challenges." Physical medicine and rehabilitation clinics of North America 30.2 (2019): 459-471. (Year: 2019).*

Pincay, Jhonny, Luis Terán, and Edy Portmann. "Health recommender systems: a state-of-the-art review." 2019 Sixth International Conference on eDemocracy & eGovernment (ICEDEG). IEEE, 2019. (Year: 2019).*

* cited by examiner

LEARNING SYSTEM, REHABILITATION SUPPORT SYSTEM, METHOD, PROGRAM, AND TRAINED MODEL

CROSS REFERENCE TO RELATED APPLICATIONS

This application is based upon and claims the benefit of priority from Japanese patent application No. 2019-120029, filed on Jun. 27, 2019, the disclosure of which is incorporated herein in its entirety by reference.

BACKGROUND

The present disclosure relates to a learning system, a rehabilitation support system, a method, a program, and a trained model.

Trainees such as patients may use a rehabilitation support system such as a walking training apparatus when they perform rehabilitation. As an example of the walking training apparatus, Japanese Patent No. 6052234 discloses a walking training apparatus including a walking assistance apparatus that is attached to a leg of a trainee and assists the trainee in walking.

In some rehabilitation support systems, when a trainee performs rehabilitation, a training staff member such as a doctor or a physical therapist may attend the rehabilitation as an assistant for the trainee, give encouraging talks to the trainee, give a helping hand to the trainee, and/or perform a setting operation for the rehabilitation support system.

SUMMARY

Incidentally, in order to obtain good training results, the setting operation of the rehabilitation support system performed by the training staff member needs to be performed so that the rehabilitation support system can appropriately assist the trainee. Further, the timing of the setting operation, i.e., the timing at which assistance is added or ceased, or at which the degree of assistance is changed also affects the training results. Therefore, in order to perform such a setting operation, the training staff member needs to make a choice as to what kind of assistance should be given to the trainee, and determine an appropriate degree of the assistance and its timing. Further, the training staff member needs to determine what kind of encouraging talks he/she should give to the trainee and when he/she should give such talks to the trainee, and determine the timing at which he/she should give a helping hand to the trainee.

However, in the present circumstances, the training staff member makes the above-described determinations by intuition and/or knack. Further, since the years of experience and the level of proficiency vary among the training staff members, the difference in training results among the training staff members becomes considerably large. Therefore, it is desirable to provide appropriate assistance so that good training results are obtained irrespective of the level of the training staff member. For this purpose, there is a need for a technique capable of, in a rehabilitation support system, making suggestions so that the above-described determinations can be made as if they were assisted by a competent training staff member (e.g., a training staff member who is highly appreciated for his/her training results) irrespective of the actual training staff member. Further, the assistance to the trainee is not limited to those given by the training staff member. That is, it is conceivable that the assistance may be given by other kinds of training assistants such as artificial assistants. Therefore, there is a need for a technique capable of making suggestions so that the above-described determinations can be made as if they were assisted by a competent training assistant irrespective of the actual training assistant.

The present disclosure has been made in order to solve the above-described problem and provides a learning system and the like that generate a learning model capable of suggesting a desirable action to a training assistant who assists a trainee when the trainee performs rehabilitation by using a rehabilitation support system. Further, the present disclosure also provides a learning system and the like that generate a learning model capable of suggesting a desirable action to a training assistant who assists a trainee when the trainee is doing training by using a training support system.

A first exemplary aspect is a learning system including: an acquisition unit configured to acquire a classification result obtained by classifying training assistants by performing a cluster analysis for first rehabilitation data about rehabilitation performed by a trainee by using a rehabilitation support system, the first rehabilitation data including at least assistant data indicating a training assistant who assists the trainee, action data indicating an assisting action performed by the training assistant to assist the trainee, and index data indicating a degree of recovery of the trainee; and a learning unit configured to generate a learning model, the learning model being configured to input second rehabilitation data including at least the action data and output the action data for suggesting a next action to be performed by the training assistant, in which the learning unit generates the learning model by using, as teacher data, the second rehabilitation data for which pre-processing has been performed based on the classification result. In this way, it is possible to generate a learning model capable of suggesting a desirable action to a training assistant who assists a trainee when the trainee performs rehabilitation by using the rehabilitation support system.

The second rehabilitation data may include at least one of the index data and the assistant data. In this way, the index data or the assistant data can be taken into consideration in the trained model.

The learning unit may generate the learning model by using, as the teacher data, the second rehabilitation data corresponding to the training assistant included in one group in the classification result. In this way, the trained model can be generated while taking the action of the training assistant belonging to one group into consideration.

Alternatively, the learning unit may generate the learning model by using the second rehabilitation data as the teacher data, the second rehabilitation data being data in which a plurality of groups that are labeled based on the classification result are associated with the assistant data each of which corresponds to a respective one of the plurality of groups. In this way, the trained model in which the action of the training assistant is taken into consideration on a group-by-group basis can be generated.

The learning system may further include an analysis unit configured to classify the training assistants by performing the cluster analysis for the first rehabilitation data, and the acquisition unit acquires a classification result obtained by classifying the training assistants from the analysis unit. In this way, the learning system can perform processing from the analysis stage.

The first and second rehabilitation data may include trainee data indicating a feature of the trainee. In this way, the feature of the trainee can be taken into consideration in the trained model.

The trainee data may include symptom data indicating at least one of a disease and a symptom of the trainee. In this way, the symptom data can be taken into consideration in the trained model.

The action data may include at least one of data indicating an operation by which a setting value in the rehabilitation support system has been changed and data indicating an assisting action for the trainee. In this way, the setting value changing operation or the state of the assisting action can be taken into consideration in the trained model.

The data indicating the operation may include data indicating a level of skill required for performing the operation. As a result, the level of skill required for the operation can be taken into consideration in the trained model.

The learning unit may generate the learning model for each of a plurality of groups in the classification result by using, as the teacher data, the second rehabilitation data corresponding to the training assistant included in that group. In this way, a plurality of types of trained models can be generated.

The learning system may include a group designation unit configured to designate one group in the classification result, and the learning unit may generate the learning model by using, as the teacher data, the second rehabilitation data corresponding to the training assistant included in the group designated by the group designation unit. In this way, a trained model only for the designated group can be generated.

A second exemplary aspect is a learning system including: an acquisition unit configured to acquire a classification result obtained by classifying training assistants by performing a cluster analysis for first data about training performed by a trainee by using a training support system, the first data including at least assistant data indicating a training assistant who assists the trainee, action data indicating an assisting action performed by the training assistant to assist the trainee, and index data indicating a degree of an improvement in a physical function of the trainee; and a learning unit configured to generate a learning model, the learning model being configured to input second data including at least the action data and output the action data for suggesting a next action to be performed by the training assistant, in which the learning unit generates the learning model by using, as teacher data, the second data for which pre-processing has been performed based on the classification result. In this way, it is possible to generate a learning model capable of suggesting a desirable action to a training assistant who assists a trainee when the trainee performs rehabilitation by using the training support system.

A third exemplary aspect is a rehabilitation support system capable of accessing a trained model, the trained model being a learning model trained by the learning system according to the first aspect, the rehabilitation support system including: an output unit configured to output the second rehabilitation data about rehabilitation performed by a trainee by using the rehabilitation support system as an input to the trained model, and a notification unit configured to notify the training assistant assisting the trainee in the rehabilitation of the action data output from the trained model. In this way, it is possible to suggest a desirable action to a training assistant who assists a trainee when the trainee performs rehabilitation by using the rehabilitation support system.

The rehabilitation support system may include a designation unit configured to designate the training assistant who assists the trainee in the rehabilitation, and can access a classification result storage unit configured to store the classification result. Further, when the training assistant designated by the designation unit is a training assistant whose teacher data has not been adopted when the trained model is generated, the output unit outputs the second rehabilitation data and the notification unit provides a notification. In this way, it is possible to prevent unnecessary notifications from being provided to training assistants who are assumed to require no notification.

A fourth exemplary aspect is a learning method including: an acquisition step of acquiring a classification result obtained by classifying training assistants by performing a cluster analysis for first rehabilitation data about rehabilitation performed by a trainee by using a rehabilitation support system, the first rehabilitation data including at least assistant data indicating a training assistant who assists the trainee, action data indicating an assisting action performed by the training assistant to assist the trainee, and index data indicating a degree of recovery of the trainee; and a learning step of generating a learning model, the learning model being configured to input second rehabilitation data including at least the action data and output the action data for suggesting a next action to be performed by the training assistant, in which in the learning step, the learning model is generated by using, as teacher data, the second rehabilitation data for which pre-processing has been performed based on the classification result. In this way, it is possible to generate a learning model capable of suggesting a desirable action to a training assistant who assists a trainee when the trainee performs rehabilitation by using the rehabilitation support system.

A fifth exemplary aspect is a method for supporting rehabilitation (a method for operating a rehabilitation support system) in a rehabilitation support system capable of accessing a trained model, the trained model being a learning model trained by the learning method according to the fourth aspect, the method including: an outputting step of outputting, by the rehabilitation support system, the second rehabilitation data about rehabilitation performed by a trainee by using the rehabilitation support system as an input to the trained model, and a notification step of notifying, by the rehabilitation support system, the training assistant assisting the trainee in the rehabilitation of the action data output from the trained model. In this way, it is possible to suggest a desirable action to a training assistant who assists a trainee when the trainee performs rehabilitation by using the rehabilitation support system.

A sixth exemplary aspect is a program for causing a computer to perform: an acquisition step of acquiring a classification result obtained by classifying training assistants by performing a cluster analysis for first rehabilitation data about rehabilitation performed by a trainee by using a rehabilitation support system, the first rehabilitation data including at least assistant data indicating a training assistant who assists the trainee, action data indicating an assisting action performed by the training assistant to assist the trainee, and index data indicating a degree of recovery of the trainee; and a learning step of generating a learning model, the learning model being configured to input second rehabilitation data including at least the action data and output the action data for suggesting a next action to be performed by the training assistant, in which in the learning step, the learning model is generated by using, as teacher data, the second rehabilitation data for which pre-processing has been performed based on the classification result. In this way, it is possible to generate a learning model capable of suggesting a desirable action to a training assistant who assists a trainee when the trainee performs rehabilitation by using the rehabilitation support system.

A seventh exemplary aspect is a rehabilitation support program for a computer of a rehabilitation support system, the rehabilitation support system being capable of accessing a trained model, the trained model being a learning model trained by the program according to the sixth aspect, the rehabilitation support program being configured to cause the computer to perform: an outputting step of outputting the second rehabilitation data about rehabilitation performed by a trainee by using the rehabilitation support system as an input to the trained model, and a notification step of notifying the training assistant assisting the trainee in the rehabilitation of the action data output from the trained model. In this way, it is possible to suggest a desirable action to a training assistant who assists a trainee when the trainee performs rehabilitation by using the rehabilitation support system.

An eighth exemplary aspect is a trained model that is any one of a learning model trained by the learning system according to the first (or second) aspect, a learning model trained by the learning method according to the fourth aspect, and a learning model trained by the program according to the sixth aspect. In this way, it is possible to provide a trained model capable of suggesting a desirable action to a training assistant assisting who assists a trainee when the trainee performs rehabilitation (or training) by using a rehabilitation support system (or a training support system).

According to the present disclosure, it is possible to provide a learning system that generates a learning model capable of suggesting a desirable action to a training assistant who assists a trainee when the trainee performs rehabilitation by using a rehabilitation support system. Further, according to the present disclosure, it is possible to provide a rehabilitation support system using a generated trained model, a method and a program for training a trained model, a trained model, and a method and a program for rehabilitation support using a trained model. Further, the present disclosure can also be applied to training other than rehabilitation, and thereby provides similar advantageous effects in the training other than rehabilitation.

The above and other objects, features and advantages of the present disclosure will become more fully understood from the detailed description given hereinbelow and the accompanying drawings which are given by way of illustration only, and thus are not to be considered as limiting the present disclosure.

DETAILED DESCRIPTION

Hereinafter, the present disclosure will be explained through embodiments of the present disclosure. However, they are not intended to limit the scope of the present disclosure according to the claims. Further, all of the components/structures described in the embodiments are not necessarily indispensable as means for solving the problem.

First Embodiment

A first embodiment will be described hereinafter with reference to the drawings.
(System Configuration)

Figure 1:
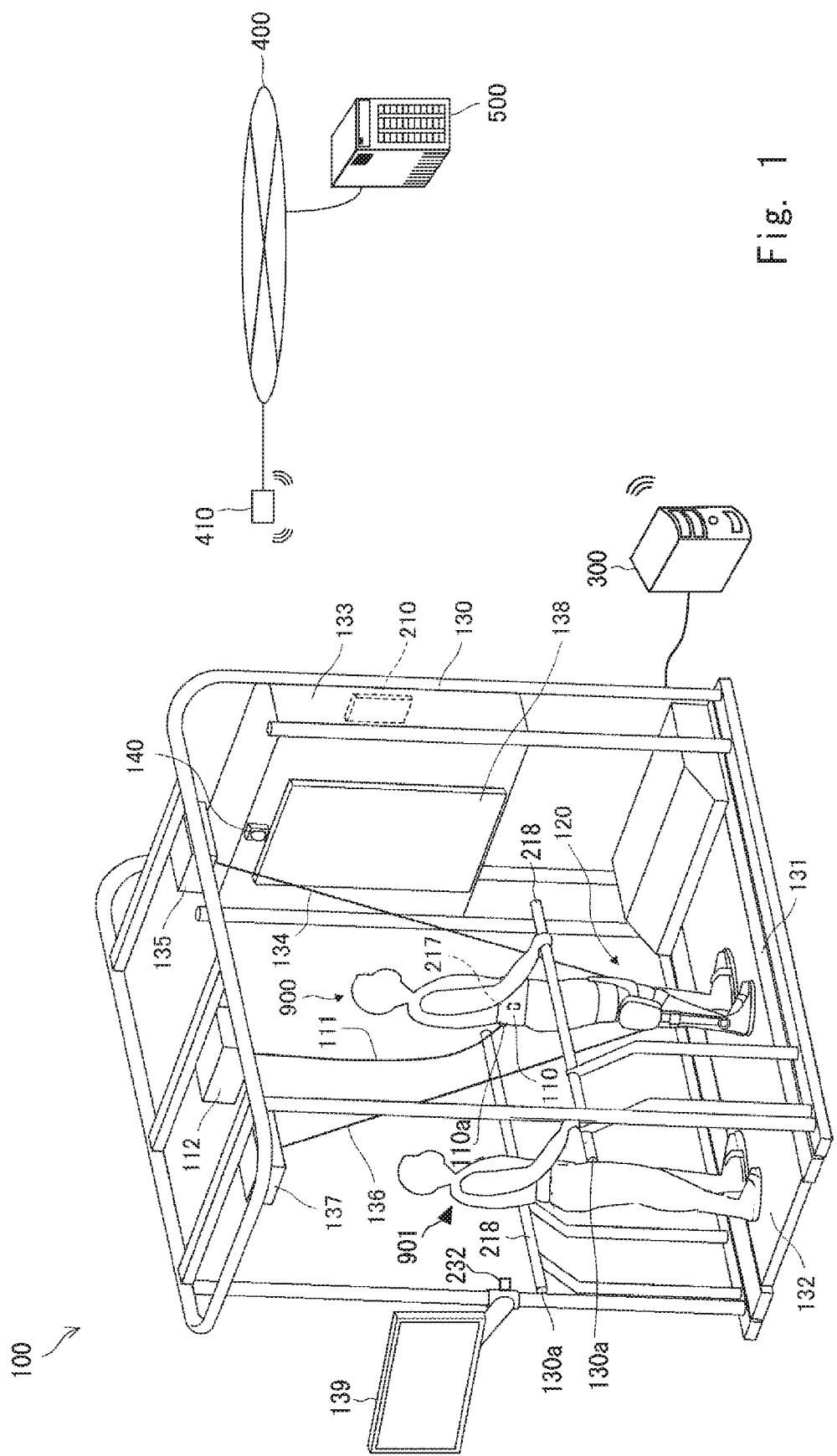
FIG. 1 is a general concept diagram showing an example of a configuration of a rehabilitation support system according to a first embodiment.

FIG. 1 is a general concept diagram showing an example of a configuration of a rehabilitation support system according to a first embodiment. The rehabilitation support system (the rehabilitation system) according to this embodiment mainly includes a walking training apparatus 100, an external communication apparatus 300, and a server (a server apparatus) 500.

The walking training apparatus 100 is a specific example of a rehabilitation support apparatus that supports rehabilitation performed by a trainee (a user) 900. The walking training apparatus 100 is an apparatus by which the trainee 900, who is, for example, a hemiplegic patient suffering from paralysis in one of his/her legs, does walking training under the guidance of a training staff member 901. Note that the training staff member 901 can be a therapist (a physical therapist) or a doctor, and may also be referred to as a training instructor, a training assistant, a training supporter, or the like because he/she instructs the trainee in training or assists the trainee by giving assistance and the like. As shown as an example above, the training staff member 901 is a person(s).

The walking training apparatus 100 mainly includes a control panel 133 attached to a frame 130 forming an overall framework, a treadmill 131 on which the trainee 900 walks, and a walking assistance apparatus 120 attached to the diseased leg, i.e., the leg on the paralyzed side of the trainee 900.

The frame 130 is disposed in a standing position on the treadmill 131 mounted on the floor surface. The treadmill 131 rotates a ring-shaped belt 132 by using a motor (not shown). The treadmill 131 is an apparatus that prompts the trainee 900 to walk, and the trainee 900, who does a walking training, gets on the belt 132 and tries walking in accordance with the movement of the belt 132. Note that the training staff member 901 can stand on the belt 132 behind the trainee 900 and walk together as shown in FIG. 1. However, the training staff member 901 may typically be in a state in which he/she can easily assists the trainee 900 such as standing with his/her feet on both sides of the belt 132.

The frame 130 supports, for example, the control panel 133 that houses an overall control unit 210 that controls motors and sensors, and a training monitor 138 that is formed by, for example, a liquid-crystal panel and shows progress of the training and the like to the trainee 900. Further, the frame 130 supports a front pulling unit 135 roughly above and in front of the head of the trainee 900, supports a harness pulling unit 112 roughly above the head, and supports a rear pulling unit 137 roughly above and behind the head. Further, the frame 130 also includes handrails 130a that the trainee 900 grasps.

The handrails 130a are disposed on the left and right sides of the trainee 900. Each of the handrails 130a is orientated in a direction parallel to the walking direction of the trainee 900. The vertical position and the left/right position of the handrails 130a are adjustable. That is, the handrails 130a may include a mechanism for changing its height and width (i.e., distance therebetween). Further, the handrails 130a can be configured so that their inclination angles can be changed by, for example, adjusting the heights of their front sides and the rear sides in the walking direction to different heights. For example, the handrails 130a can have an inclination angle so that their heights gradually increase along the walking direction.

Further, each of the handrails 130a is equipped with a handrail sensor 218 that detects a load (e.g., a pressure) received from the trainee 900. For example, the handrail sensor 218 may be a resistance change detection-type load detection sheet in which electrodes are arranged in a matrix pattern. Further, the handrail sensor 218 may be a six-axis sensor in which a three-axis acceleration sensor (x, y, z) is combined with a three-axis gyro sensor (roll, pitch, yaw). However, there is no particular limitation on the type of the handrail sensor 218 and the place where the handrail sensor 218 is disposed.

The camera 140 functions as an image pickup unit for observing the whole body of the trainee 900. The camera 140 is disposed near the training monitor 138 and positioned so as to face the trainee. The camera 140 takes still images and/or moving images of the trainee 900 during the training. The camera 140 includes a set of a lens and an image pickup device so that it has such an angle of view that it can shoot the whole body of the trainee 900. The image pickup device is, for example, a CMOS (Complementary Metal-Oxide-Semiconductor) image sensor, and converts an optical image formed on an image forming surface into an image signal.

By the coordinated operation of the front pulling unit 135 and the rear pulling unit 137, the load of the walking assistance apparatus 120 is cancelled so that it does not become a load on the diseased leg. Further, the swinging motion of the diseased leg is assisted according to the set level.

One end of a front wire 134 is connected to a winding mechanism of the front pulling unit 135 and the other end thereof is connected to the walking assistance apparatus 120. The winding mechanism of the front pulling unit 135 winds or pays out the front wire 134 according to the motion of the diseased leg by turning on/off a motor (not shown). Similarly, one end of a rear wire 136 is connected to the winding mechanism of the rear pulling unit 137 and the other end thereof is connected to the walking assistance apparatus 120. The winding mechanism of the rear pulling unit 137 winds or pays out the rear wire 136 according to the motion of the diseased leg by turning on/off a motor (not shown). By the coordinated operation of the front pulling unit 135 and the rear pulling unit 137 as described above, the load of the walking assistance apparatus 120 is cancelled so that it does not become a load on the diseased leg. Further, the swinging motion of the diseased leg is assisted according to the set level.

For example, the training staff member 901, who serves as an operator, increases the set assistance level for a trainee who suffers from severe paralysis. When the assistance level is set to a large value, the front pulling unit 135 winds the front wire 134 with a relatively large force according to the timing of the swinging of the diseased leg. When the training has progressed and the assistance is no longer required, the training staff member 901 sets the assistance level to the minimum value. When the assistance level is set to the minimum value, the front pulling unit 135 winds the front wire 134 according to the timing of the swinging of the diseased leg with a force by which only the weight of the walking assistance apparatus 120 itself is cancelled.

The walking training apparatus 100 includes a fall-prevention harness apparatus as a safety apparatus, which includes, as its main components, a harness 110, a harness wire 111, and a harness pulling unit 112. The harness 110 is a belt that is wound around the abdomen of the trainee 900 and is fixed to his/her waist by, for example, a hook-and-loop fastener. The harness 110 includes a connection hook 110a that connects one end of the harness wire 111, which serves as a hoisting tool, to the harness 110, and may be referred to as a hanger belt. The trainee 900 attaches the harness 110 to his/her diseased leg so that the connection hook 110a is positioned in the rear part of the diseased leg.

One end of the harness wire 111 is connected to the connection hook 110a of the harness 110 and the other end thereof is connected to a winding mechanism of the harness pulling unit 112. The winding mechanism of the harness pulling unit 112 winds or pays out the harness wire 111 by turning on/off a motor (not shown). By the above-described configuration, when the trainee 900 is about to fall down, the fall-prevention harness apparatus winds the harness wire 111 according to an instruction from the overall control unit 210, which has detected the falling-down movement of the trainee 900, and thereby supports the upper body of the trainee 900 by the harness 110, so that the trainee 900 is prevented from falling down.

The harness 110 includes a posture sensor 217 for detecting the posture of trainee 900. The posture sensor 217 is, for example, a combination of a gyro sensor and an acceleration sensor, and outputs an inclination angle of the abdomen, to which the harness 110 is attached, with respect to the direction of gravity.

A management monitor 139 is attached to the frame 130 and serves as a display/input device by which the training staff member 901 or the like monitors and operates the rehabilitation support system. The management monitor 139 is formed by, for example, a liquid crystal panel. Further, a touch panel is disposed over its surface. The management monitor 139 displays various menu items related to the training setting, various parameter values during the training, training results, and so on. Further, an emergency stop button 232 is provided near the management monitor 139. When the training staff member 901 pushes the emergency stop button 232, the walking training apparatus 100 immediately stops its operation.

The walking assistance apparatus 120 is attached to the diseased leg of the trainee 900 and assists the trainee 900 in walking by reducing the load of the extension and flexion at the knee joint of the diseased leg. The walking assistance apparatus 120 includes a sensor or the like that measures the load (e.g., the pressure) on the sole of the foot, and outputs various data related to the moving leg to the overall control unit 210. Further, the harness 110 can be connected to the walking assistance apparatus 120 by using a connection member (hereinafter referred to as a hip joint) including a rotation part. Details of the walking assistance apparatus 120 will be described later.

The overall control unit 210 generates rehabilitation data that may include setting parameters related to the training setting, various data related to the moving leg output from the walking assistance apparatus 120 as a result of training, and so on. The rehabilitation data may include, for example, data indicating the training staff member 901 or indicating his/her years of experience, level of proficiency, etc., data indicating the symptom, the walking ability, the degree of recovery, etc., of the trainee 900, various data output from sensors and the like provided outside the walking assistance apparatus 120. Note that details of the rehabilitation data will be described later.

The external communication apparatus 300 is a specific example of transmission means for transmitting the rehabilitation data to the outside. The external communication apparatus 300 may have a function of receiving and temporarily storing rehabilitation data output from the walking training apparatus 100 and a function of transmitting the stored rehabilitation data to the server 500.

The external communication apparatus 300 is connected to the control panel 133 of the walking training apparatus 100 through, for example, a USB (Universal Serial Bus) cable. Further, the external communication apparatus 300 is connected to a network 400 such as the Internet or an intranet through a wireless communication apparatus 410 by, for example, a wireless LAN (Local Area Network). Note that the walking training apparatus 100 may be equipped with a communication apparatus instead of using the external communication apparatus 300.

The server 500 is a specific example of the storage means for storing rehabilitation data. The server 500 is connected to the network 400 and has a function of accumulating rehabilitation data received from the external communication apparatus 300. The function of the server 500 will be described later.

In the first embodiment, the walking training apparatus 100 is described as an example of the rehabilitation support apparatus. However, the rehabilitation support apparatus is not limited to this example and may be a walking training apparatus having a different configuration. That is, the rehabilitation support apparatus may be an arbitrary rehabilitation support apparatus that supports rehabilitation performed by a trainee. For example, the rehabilitation support apparatus may be an upper-limb rehabilitation support apparatus that supports rehabilitation of a shoulder(s) or an arm(s). Alternatively, the rehabilitation support apparatus may be a rehabilitation support apparatus that supports rehabilitation for a balancing ability of a trainee.

Figure 2:
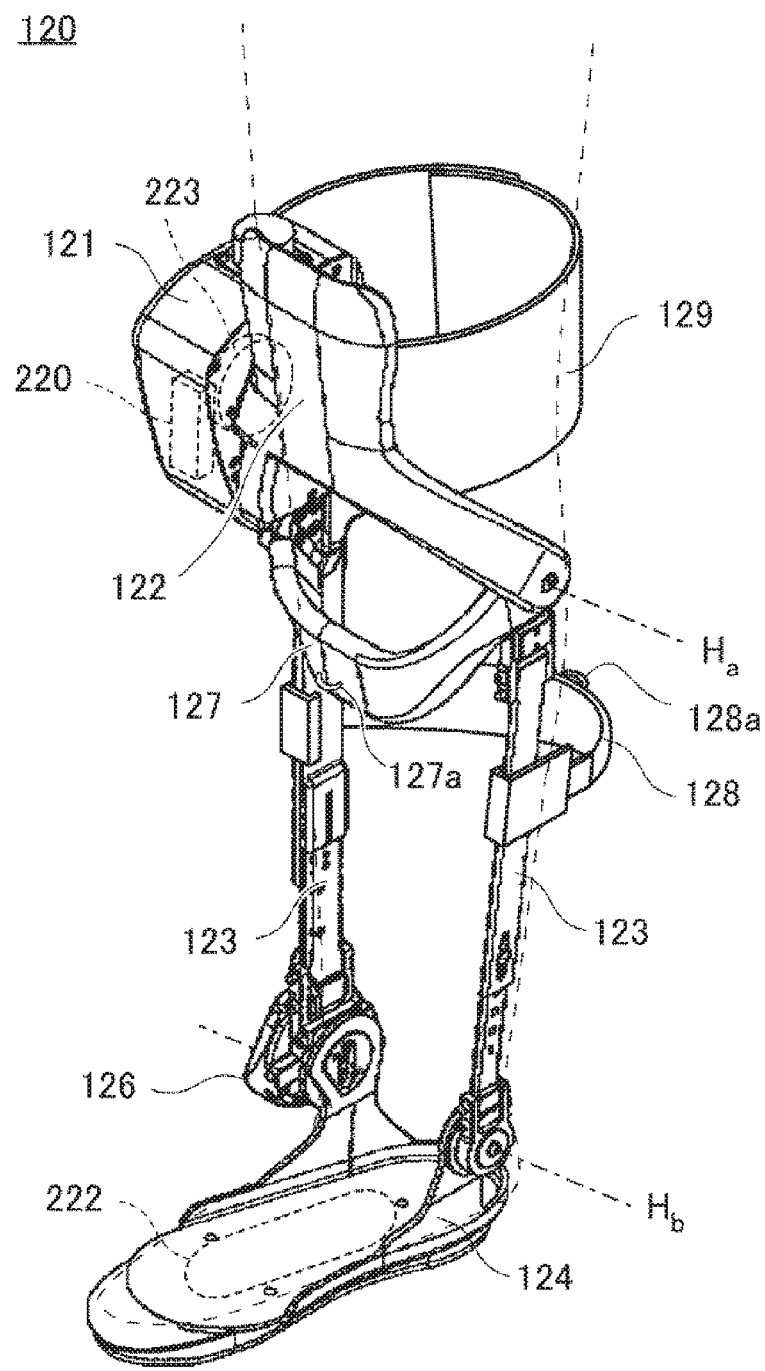
FIG. 2 is a schematic perspective view showing an example of a configuration of a walking assistance apparatus in the rehabilitation support system shown in FIG. 1.

Next, the walking assistance apparatus 120 will be described with reference to FIG. 2. FIG. 2 is a schematic perspective view showing an example of a configuration of the walking assistance apparatus 120. The walking assistance apparatus 120 mainly includes a control unit 121, a plurality of frames that support each part of a diseased leg, and a load sensor 222 for detecting a load (e.g., a pressure) applied to the sole.

The control unit 121 includes an assistance control unit 220 that controls the walking assistance apparatus 120, and also includes a motor(s) (not shown) that generates a driving force(s) for assisting extending movements and flexing movements of the knee joint. The frames, which support each part of the diseased leg, includes an upper-leg frame 122 and a lower-leg frame 123 rotatably connected to the upper-leg frame 122. Further, the frames also include a sole frame 124 rotatably connected to the lower-leg frame 123, a front connection frame 127 for connecting a front wire 134, and a rear connection frame 128 for connecting a rear wire 136.

The upper-leg frame 122 and the lower-leg frame 123 rotate relative to each other around a hinge axis $H_a$ shown in the figure. The motor of the control unit 121 rotates according to an instruction from the assistance control unit 220, and by doing so, force the upper-leg frame 122 and the lower-leg frame 123 to open relative to each other around the hinge axis $H_a$ or force them to close relative to each other. The angle sensor 223 housed in the control unit 121 is, for example, a rotary encoder and detects an angle between the upper-leg frame 122 and the lower-leg frame 123 around the hinge axis $H_a$. The lower-leg frame 123 and the sole frame 124 rotate relative to each other around a hinge axis $H_b$ shown in the figure. The angular range of their relative rotation is adjusted in advance by an adjustment mechanism 126.

The front connection frame 127 is disposed so as to extend in the left/right direction in front of the upper leg and is connected to the upper-leg frame 122 at both ends. Further, a connection hook 127a for connecting the front wire 134 is provided at or near the center of the front connection frame 127 in the left/right direction. The rear connection frame 128 is disposed so as to extend in the left/right direction behind the lower leg and is connected to the lower-leg frame 123 at both ends. Further, a connection hook 128a for connecting the rear wire 136 is provided at or near the center of the rear connection frame 128 in the left/right direction.

The upper-leg frame 122 includes an upper-leg belt 129. The upper-leg belt 129 is a belt integrally provided in the upper-leg frame and is wound around the upper leg of the diseased leg to fix the upper-leg frame 122 to the upper leg. In this way, the whole walking assistance apparatus 120 is prevented from being displaced from the leg of the trainee 900.

The load sensor 222 is a load sensor embedded in the sole frame 124. The load sensor 222 may be configured to detect a magnitude and a distribution of a vertical load (e.g., a vertical pressure) received by the sole of the trainee 900. For example, the load sensor 222 may be configured to detect a COP (Center Of Pressure) of the sole. The load sensor 222 is, for example, a resistance change detection-type load detection sheet in which electrodes are arranged in a matrix pattern.

Figure 3:
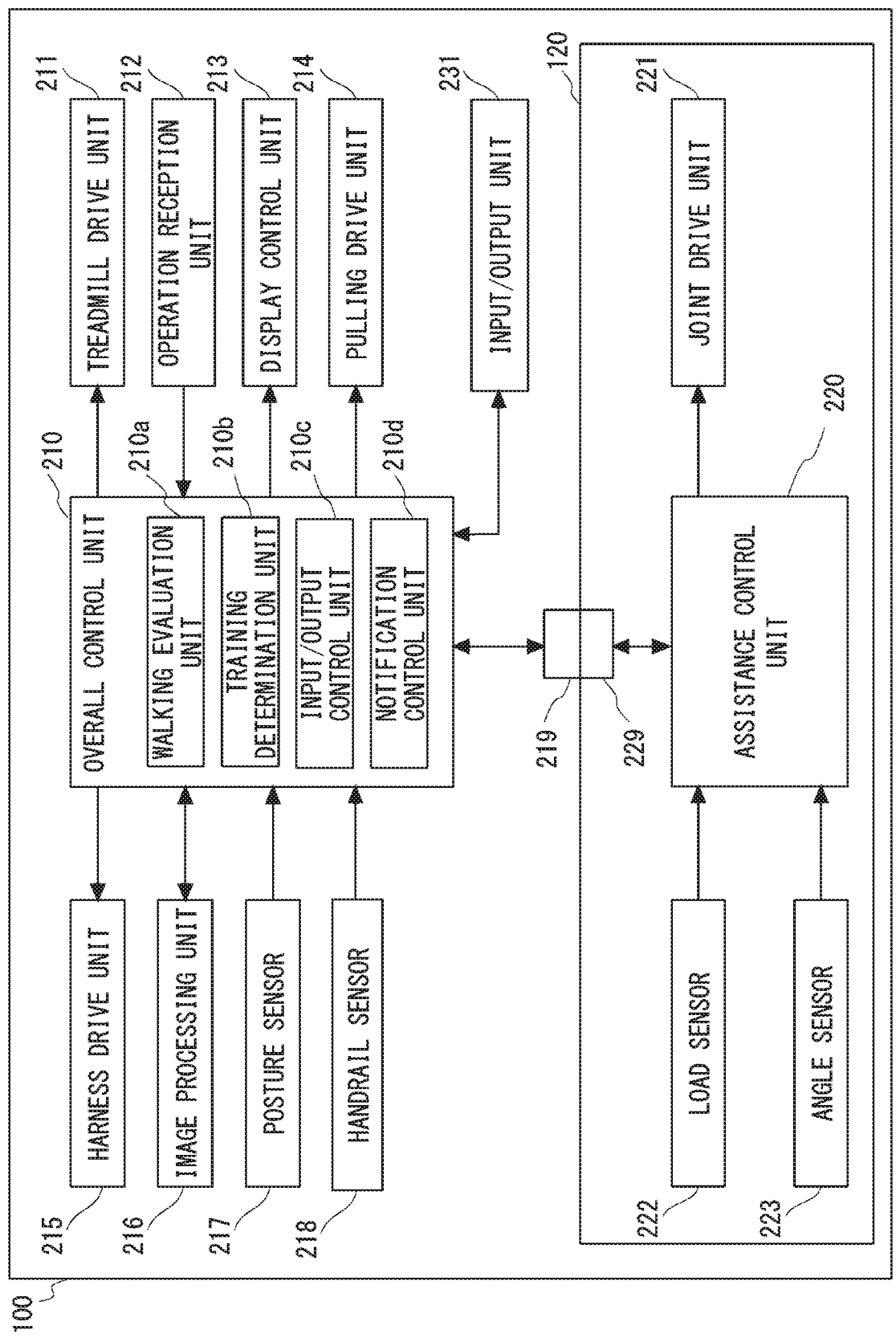
FIG. 3 is a block diagram showing an example of a system configuration of a walking training apparatus in the rehabilitation support system shown in FIG. 1.

Next, an example of a system configuration of the walking training apparatus 100 will be described with reference to FIG. 3. FIG. 3 is a block diagram showing an example of a system configuration of the walking training apparatus 100. As shown in FIG. 3, the walking training apparatus 100 may include an overall control unit 210, a treadmill drive unit 211, an operation reception unit 212, a display control unit 213, and a pulling drive unit 214. Further, the walking training apparatus 100 may include a harness drive unit 215, an image processing unit 216, a posture sensor 217, a handrail sensor 218, a communication connection IF (interface) 219, an input/output unit 231, and a walking assistance apparatus 120.

The overall control unit 210 is, for example, an MPU (Micro Processing Unit) and controls the overall operations of the apparatus by executing a control program loaded from a system memory. The overall control unit 210 may include a walking evaluation unit 210a, a training determination unit 210b, an input/output control unit 210c, and a notification control unit 210d, all of which will be described later.

The treadmill drive unit 211 includes a motor that rotates the belt 132 and its drive circuit. The overall control unit 210 controls the rotation of the belt 132 by sending a drive signal to the treadmill drive unit 211. The overall control unit 210 adjusts, for example, the rotational speed of the belt 132 according to a walking speed set by the training staff member 901.

The operation reception unit 212 receives an input operation from the training staff member 901 and transmits an operation signal to the overall control unit 210. The training staff member 901 operates operation buttons provided in the apparatus, a touch panel disposed over the management monitor 139, an accessory remote controller, etc., which constitute the operation reception unit 212. By the above-described operation, the training staff member can turn on/off the power, provide an instruction to start training, enter a numerical value for the setting, and select a menu item. Note that the operation reception unit 212 can also receive an input operation from the trainee 900.

The display control unit 213 receives a display signal from the overall control unit 210, generates a display image, and displays the generated display image on the training monitor 138 or the management monitor 139. The display control unit 213 generates an image showing progress of the training and a real-time video image shot by the camera 140.

The pulling drive unit 214 includes a motor for pulling the front wire 134 and its drive circuit, which constitute the front pulling unit 135, and a motor for pulling the rear wire 136 and its drive circuit, which constitute the rear pulling unit 137. The overall control unit 210 controls winding of the front wire 134 and winding of the rear wire 136 by sending a drive signal(s) to the pulling drive unit 214. Further, the pulling force of each wire is controlled by controlling the driving torque of the respective motor in addition to controlling the winding operation. The overall control unit 210 identifies (i.e., determines), for example, a timing at which the diseased leg changes from a stance state to a swing state from the result of the detection by the load sensor 222, and assists the swinging action of the diseased leg by increasing or decreasing the pulling force of each wire in synchronization with the identified timing.

The harness drive unit 215 includes a motor for pulling the harness wire 111 and its drive circuit, which constitute the harness pulling unit 112. The overall control unit 210 controls winding of the harness wire 111 and the pulling force of the harness wire 111 by sending a drive signal(s) to the harness drive unit 215. For example, when the overall control unit 210 predicts that the trainee 900 will fall down, it prevents the trainee from falling down by winding the harness wire 111 by a certain length.

The image processing unit 216 is connected to the camera 140, so that it can receive an image signal from the camera 140. The image processing unit 216 receives an image signal from the camera 140 according to an instruction from the overall control unit 210, and generates image data by performing image processing on the received image signal. Further, the image processing unit 216 can also perform a specific image analysis by performing image processing on the image signal received from the camera 140 according to an instruction from the overall control unit 210. For example, the image processing unit 216 detects the position of the foot of the diseased leg at which the foot is in contact with the treadmill 131 (i.e., a stance position) by the image analysis. Specifically, for example, the image processing unit 216 extracts an image area near the tip of the sole frame 124, and calculates the stance position by analyzing an identification marker drawn on a part of the belt 132 where the tip of the sole frame 124 is located.

The posture sensor 217 detects an inclination angle of the abdomen of the trainee 900 with respect to the direction of gravity as described above, and transmits a detection signal to the overall control unit 210. The overall control unit 210 calculates the posture of the trainee 900, in particular, an inclination angle of his/her trunk by using the detection signal from the posture sensor 217. Note that the overall control unit 210 and the posture sensor 217 may be connected to each other through a cable or through short-range wireless communication.

The handrail sensor 218 detects a load (e.g., a pressure) applied to the handrail 130a. That is, the amount of the load corresponding to the part of the trainee's own weight that the trainee 900 cannot support by both legs is applied to the handrails 130a. The handrail sensor 218 detects this load and transmits a detection signal to the overall control unit 210.

The overall control unit 210 also serves as a function execution unit that performs various arithmetic operations and controls related to the overall control. The walking evaluation unit 210a evaluates whether the walking motion of the trainee 900 is abnormal or not by using data acquired from various sensors. The training determination unit 210b determines a training result of a series of walking trainings based on, for example, a cumulative number of the abnormal walking evaluated by the walking evaluation unit 210a. The overall control unit 210 can generate, as part of the rehabilitation data, a result of this determination or the cumulative number of the abnormal walking, based on which the determination result has been obtained.

Note that the determination method, including its criterion, is not limited to any particular methods. For example, the determination can be made by comparing an amount of movement of the paralyzed body part with a reverence value in each walking phase. Note that the walking phases are defined, for example, by classifying (i.e., dividing) one walking cycle of the diseased leg (or a normal leg) into a stance phase in a stance state, a transition phase from the stance phase to a swing phase in a swing state, the swing phase, a transition phase from the swing phase to the stance phase, etc. The walking phase can be classified (determined) based on, for example, the detection result of the load sensor 222 as described above. Note that although the walking cycle can be regarded as one cycle including a stance phase, a transitional phase, a swing phase, and another transitional phase as described above, any of these phases can be defined as the start phase. Alternatively, the walking cycle can be regarded as one cycle including, for example, a double-leg support state, a single-leg (diseased-leg) support state, a double-leg support state, and a single-leg (normal-leg) support state. Even in this case, any state may be defined as the start state.

Further, the walking cycle in which attention is paid to the right leg or the left leg (the normal leg or the diseased leg) can be further subdivided. For example, the stance phase can be divided into an initial ground contact and other four sub-phases, and the swing phase can be divided into three sub-phases. The initial ground contact means a moment when the observed foot touches the floor, and the four sub-phases of the stance phase means a load response phase, a mid-stance phase, a terminal stance phase, and a pre-swing phase. The load response phase is a period from the initial ground contact to when the opposite foot comes off the floor (opposite-foot-off). The mid-stance is a period from the opposite-foot-off to when the heel of the observed foot comes off the floor (heel-off). The terminal stance phase is a period from the heel-off to an initial ground contact on the opposite side. The pre-swing phase is a period from the initial ground contact on the opposite side to when the observed foot comes off the floor (foot-off). The three sub-phases of the swing phase mean an initial swing phase, a mid-swing phase, and a terminal swing phase. The initial swing phase is a period from the end of the pre-swing phase (the aforementioned foot-off) to when both feet cross each other (foot crossing). The mid-swing phase is a period from the foot crossing to when the tibia becomes vertical (vertical tibia). The terminal swing phase is a period from the vertical tibia to the next initial ground contact.

The communication connection IF 219 is an interface connected to the overall control unit 210, and is an interface for providing an instruction to the walking assistance apparatus 120 attached to the diseased leg of the trainee 900 and receiving sensor information therefrom.

The walking assistance apparatus 120 may include a communication connection IF 229 that is connected to the communication connection IF 219 through a cable or wirelessly. The communication connection IF 229 is connected to the assistance control unit 220 of the walking assistance apparatus 120. The communication connection IFs 219 and 229 are communication interfaces in conformity with communication standards, such as those of a wired LAN or a wireless LAN.

Further, the walking assistance apparatus 120 may include an assistance control unit 220, a joint drive unit 221, a load sensor 222, and an angle sensor 223. The assistance control unit 220 is, for example, an MPU and controls the walking assistance apparatus 120 by executing a control program according to an instruction from the overall control unit 210. Further, the assistance control unit 220 notifies the overall control unit 210 of the state of the walking assistance apparatus 120 through the communication connection IFs 229 and 219. Further, the assistance control unit 220 performs control of walking assistance apparatus 120, such as the start/stop thereof, in response to a command from the overall control unit 210.

The joint drive unit 221 includes a motor of the control unit 121 and its drive circuit. The assistance control unit 220 sends a drive signal to the joint drive unit 221 to force the upper-leg frame 122 and the lower-leg frame 123 to open relative to each other around the hinge axis $H_a$ or force them to close relative to each other. Through the above-described operations, the assistance control unit 220 assists an extending motion and a flexing motion of the knee and prevents the knee from buckling.

The load sensor 222 detects the magnitude and the distribution of the vertical load (e.g., the vertical pressure) applied to the sole of the trainee 900 and transmits a detection signal to the assistance control unit 220 as described above. The assistance control unit 220 receives and analyzes the detection signal, and thereby determines the swing/stance state and estimates the switching therebetween.

The angle sensor 223 detects the angle between the upper-leg frame 122 and the lower-leg frame 123 around the hinge axis $H_a$ and transmits a detection signal to the assistance control unit 220 as described above. The assistance control unit 220 receives this detection signal and calculates the open angle of the knee joint.

The input/output unit 231 includes, for example, a USB (Universal Serial Bus) interface and is a communication interface for connecting to an external apparatus (an external communication apparatus 300 or other external apparatus). The input/output control unit 210c of the overall control unit 210 communicates with the external apparatus through the input/output unit 231, rewrites the above-described control program stored in the overall control unit 210 and the control program stored in the assistance control unit 220, receives commands, outputs generated rehabilitation data, and so on. The walking training apparatus 100 communicates with the server 500 through the input/output unit 231 and the external communication apparatus 300 under the control of the input/output control unit 210c. For example, the input/output control unit 210c can control the transmission of rehabilitation data to the server 500 and the reception of a command from the server 500 through the input/output unit 231 and the external communication apparatus 300.

When it is necessary to provide a notification to the training staff member 901, the notification control unit 210d provides the notification from the management monitor 139 or a separately-provided speaker(s) by controlling the display control unit 213 or a separately-provided sound control unit or the like. The aforementioned situation where it is necessary to provide a notification to the training staff member 901 may be a situation where a command for providing a notification is received from the server 500. Details of this notification will be described later.

Next, the server 500 will be described in detail. As described above, the walking training apparatus 100 transmits various rehabilitation data to the server 500 through the external communication apparatus 300. The server 500 may be configured so as to receive rehabilitation data from a plurality of walking training apparatuses 100. In this way, the server 500 can collect a number of rehabilitation data. Further, the server 500 is a processing apparatus that processes various data. For example, the server 500 can function as a learning apparatus (a learning system) that constructs a trained model by performing machine learning by using collected rehabilitation data. The learning apparatus can also be a learning machine. Note that the learning apparatus may also be referred to as a learning model generation apparatus.

Figure 4:
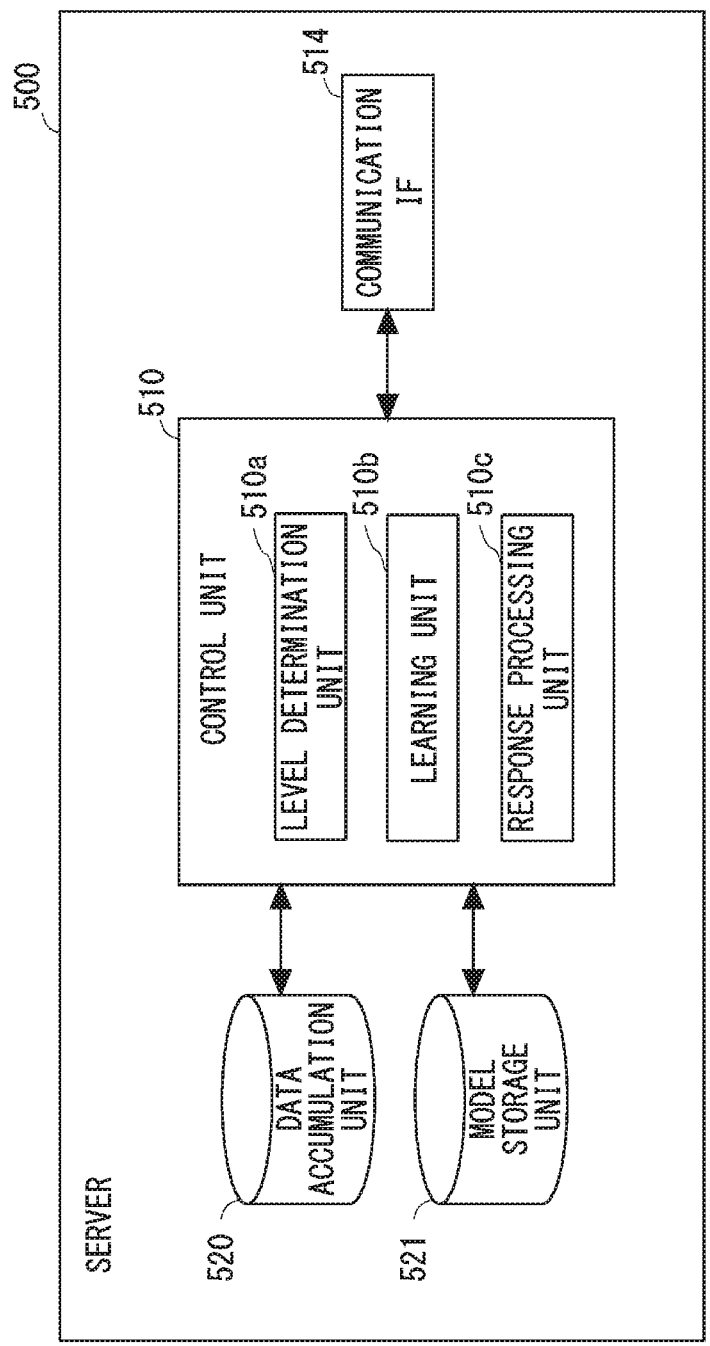
FIG. 4 is a block diagram showing an example of a configuration of a server in the rehabilitation support system shown in FIG. 1.

FIG. 4 is a block diagram showing an example of a configuration of the server 500. As shown in FIG. 4, the server 500 may include a control unit 510, a communication IF 514, a data accumulation unit 520, and a model storage unit 521. The control unit 510 is, for example, an MPU and controls the server 500 by executing a control program loaded from a system memory. The control unit 510 may include a level determination unit 510a, a learning unit 510b, and a response processing unit 510c, which will be described later. Further, in this case, the above-described control program includes a program(s) for implementing the functions of the aforementioned units 510a to 510c.

The communication IF 514 includes, for example, a wired LAN interface and is a communication interface for connecting to the network 400. The control unit 510 can receive rehabilitation data from the walking training apparatus 100 and transmit a command to the walking training apparatus 100 through the communication IF 514.

The data accumulation unit 520 includes a storage device such as an HDD (hard disk drive) or an SSD (solid state drive) and stores rehabilitation data therein. The control unit 510 writes the rehabilitation data received from the external communication apparatus 300 into the data accumulation unit 520 through the communication IF 514.

Similarly, the model storage unit 521 includes a storage device such as an HDD or an SSD. Note that the data accumulation unit 520 and the model storage unit 521 may include (i.e., share) a common storage device. The model storage unit 521 stores at least one of a learning model that has not been trained yet (including those under training) (hereinafter referred to as an untrained model) and a learning model that has been already trained (hereinafter referred to as a trained model). When the server 500 functions as a learning apparatus, at least an untrained model is stored in the model storage unit 521. When the server 500 performs a rehabilitation support process in cooperation with the walking training apparatus 100, at least an operable trained model is stored in the model storage unit 521.

Further, the control unit 510 may be configured so as to perform control to switch between a function as a learning apparatus and a function for performing a rehabilitation support process by using a trained model. Note that the servers 500 may be distributed to (or divided into) an apparatus that is used in a learning stage and an apparatus that is used in an operation stage in which a trained model is used. The level determination unit 510a and the learning unit 510b are provided in order to enable the server 500 to function as a learning apparatus. Further, the response processing unit 510c is provided in order to enable the server 500 to perform a part of the rehabilitation support process.

(Rehabilitation Data)

Prior to describing the level determination unit 510a, the learning unit 510b, and the response processing unit 510c, rehabilitation data that the server 500 can collect for learning or for a rehabilitation support process is described hereinafter. The rehabilitation data that the server 500 can collect mainly includes (1) setting parameters of the walking training apparatus 100, (2) detection data detected by sensors and the like provided in the walking training apparatus 100, (3) data related to the trainee 900, and (4) data related to the training staff member 901. The rehabilitation data of the above-described items (1) to (4) may be collected in association with their acquisition date. Further, the detection data or the setting parameter may be collected as time-series log data, or may be, for example, feature values extracted from data acquired at certain time intervals.

The rehabilitation data is mainly data that is obtained by an input operation, an automatic input, a measurement by a sensor, or the like in the walking training apparatus 100. Further, the rehabilitation data may also include recorded image data recorded by the camera 140. Note that the rehabilitation data may be data acquired on each day of rehabilitation. In this case, the rehabilitation data can be referred to as daily report data. In the following description, it is assumed that the server 500 collects rehabilitation data generated by the walking training apparatus 100. However, it is also possible to configure the server 500 so as to acquire a part of rehabilitation data from an apparatus other than the walking training apparatus 100 such as another server. Here, the part of the rehabilitation data may be, for example, a detail of data of the above-described item (3) such as a symptom of the trainee 900, or a detail of data of the above-described item (4) such as years of experience of a PT (Physical Therapist). The former can be stored in other servers as medical record information of the trainee 900 and the latter can be stored in other servers as a personal history of a PT.

In the learning stage, the server 500 may receive rehabilitation data from the walking training apparatus 100 when new rehabilitation data is generated or at regular intervals such as on every day or in every week. The type of rehabilitation data to be used (the content included in rehabilitation data) in the learning stage may be changed from that in the operation stage. For example, in the operation stage, the server 500 may receive rehabilitation data from the walking training apparatus 100 at the start of training, and may receive data of the above-described item (1) and (2) that is changed during the training. Further, the transmission and the reception of rehabilitation data may be initiated by either the walking training apparatus 100 or the server 500.

The above-described item (1) is described.

The data of the above-described item (1) can be defined as training data of the trainee 900 that is acquired during rehabilitation in the walking training apparatus 100 together with the detection data of the above-described item (2).

The setting parameter of the walking training apparatus 100 is, for example, data that is input by an operator or automatically set in order to define the actions performed by the walking training apparatus 100. Note that as described above, it is assumed that the operator is typically the training staff member 901 who actually attends the training of the trainee 900. Therefore, the following description is given on the assumption that the operator is the training staff member 901. Further, the training staff member 901 is often a PT (Physical Therapist). Therefore, the training staff member 901 may also be referred to simply as the "PT" in the following description.

In the walking training apparatus 100, the level of difficulty of walking training can be adjusted by the setting parameters. Note that the setting parameters may include a parameter indicating the level of difficulty, and in this case, some or all of the other setting parameters may be changed according to the change in the level of difficulty. The training staff member 901 increases the level of difficulty of the walking training as the trainee 900 recovers. That is, the training staff member 901 reduces the assistance provided by the walking training apparatus 100 as the walking ability of the trainee 900 improves. Further, the training staff member 901 increases the assistance when an abnormality is found during the walking training. As the training staff member 901 appropriately adjusts the setting parameters, the trainee 900 can perform appropriate walking training and hence perform the rehabilitation more efficiently.

Specific examples of the setting parameters are shown hereinafter. Examples of the setting parameters include a partial weight-supported amount [%], vertical positions of the handrails 130a [cm], left/right positions of the handrails 130a [cm], presence/absence of a hip joint, ankle joint plantar flexion limitation [deg], and ankle joint dorsiflexion limitation [deg]. Further, the examples of the setting parameters also include a treadmill speed [km/h], swinging assistance [level], and a swinging forward/backward ratio [forward/backward]. Further, the examples of the setting parameters also include knee extension assistance [level], a knee flexing angle [deg], a knee flexing/extending time [sec], a wedge thickness (or a shoe lift) [mm], a weight-off threshold [%], and a load threshold [%]. Further, the examples of the setting parameters also include an inclination of the belt of the treadmill [deg], assistance for a motion of a joint by the walking assistance apparatus [level], a frequency with which assistance for a motion of a joint or swinging assistance by the walking assistance apparatus is provided, a condition for determining abnormal or normal walking (e.g., a determination threshold), a condition for determining that the trainee will fall down or is likely to fall down (e.g., a determination threshold), and a condition for an occurrence of abnormal or normal walking in the case where a notification is provided in association with the abnormal or normal walking (a frequency of occurrences, an occurrence threshold, etc.). Note that the notification may be any of a sound, a vibration, a display, or the like, and may include some or all of them. Note that any type of unit may be used as the unit of data included in rehabilitation data, including the above-shown setting parameters.

The partial weight-supported amount is a ratio at which the weight of the trainee 900 is supported by making the harness pulling unit 112 pull the harness wire 111. The training staff member 901 sets the partial weight-supported amount to a lower value as the desired level of difficulty of the walking training increases. The vertical positions and the left/right positions of the handrails 130*a* are amounts of adjustments of the handrails 130*a* from reference positions. The presence/absence of a hip joint is whether or not the hip joint is attached. The ankle joint plantar flexion limitation and the ankle joint dorsiflexion limitation define an angular range in which the lower-leg frame 123 and the sole frame 124 can rotate around the hinge axis $H_b$. The ankle joint plantar flexion limitation corresponds to an upper-limit angle on the front side and the ankle joint dorsiflexion limitation corresponds to a maximum angle on the rear side. That is, the ankle joint plantar flexion limitation and the ankle joint dorsiflexion limitation are limit values of angles at which the ankle joint is bent in a direction in which the toe is lowered and a direction in which the toe is raised, respectively. The training staff member 901 sets the values of the ankle joint plantar flexion limitation and the ankle joint dorsiflexion limitation so that the angular range increases as the desired level of difficulty of the walking training increases.

The treadmill speed is a walking speed on the treadmill 131. The training staff member 901 sets the treadmill speed to a higher value as the desired level of difficulty of the walking training increases. The swinging assistance is a level corresponding to the pulling force applied by the front wire 134 when the leg is swung. Further, the maximum pulling force is increased as this level is raised. The training staff member 901 sets the swinging assistance to a lower level as the desired level of difficulty of the walking training increases. The swinging forward/backward ratio is a ratio between the pulling force by the front wire 134 and the pulling force by the rear wire 136 when the leg is swung.

The knee extending assistance is a level corresponding to the driving torque of the joint drive unit 221 that is applied to prevent the knee from buckling during the stance state. Further, the driving torque is increased as this level is raised. The training staff member 901 sets the knee extending assistance at a lower level as the desired level of difficulty of the walking training increases. The knee flexing angle is an angle at which knee extending assistance is provided. The knee flexing/extending time is a period during which the knee extending assistance is provided. Further, when this value is large, the knee is assisted so that it is slowly flexed and extended, whereas when this value is small, the knee is assisted so that it is quickly flexed and extended.

The wedge thickness is a height of a member such as a cushion provided in the sole of the shoe of the leg of the trainee 900 opposite to the paralyzed leg thereof (i.e., the leg on the side on which the walking assistance apparatus 120 is not attached). The weight-off threshold is one of the thresholds for the load (i.e., the pressure) applied to the sole. When the load becomes smaller than this threshold, the swinging assistance is cancelled (i.e., ceased). The load threshold is one of the thresholds for the load applied to the sole. When the load exceeds this threshold, the swinging assist is provided (i.e., started). As described above, the walking assistance apparatus 120 may be configured so that the flexing/extending motion of the knee can be adjusted by four setting parameters, i.e., the knee flexing angle, the knee flexing/extending time, the weight-off threshold, and the load threshold.

Further, the walking training apparatus 100 may also be configured so that setting values of various parameters such as a load and an angle, a target value, a target achievement rate, a target achievement timing, etc. are fed back to the trainee and/or training staff member by a sound output from a speaker(s) (not shown). The above-described setting parameters may include parameters for other settings such as presence/absence of a feedback sound and its volume.

Further, the above-described setting parameters may not be setting parameters directly related to the training. For example, the above-described setting parameters may be setting values for images, music, a type of game, a level of difficulty of game, etc. that are provided through the training monitor 138 or a speaker(s) (not shown) in order to motivate the trainee 900.

Note that the above-described setting parameters are merely examples and other setting parameters may be used. Further, some of the above-described setting parameters may not be used. Further, although the above-described setting parameters include many parameters for adjusting the level of difficulty of the training as described above, they may also include parameters unrelated to the level of difficulty. For example, the walking training apparatus 100 may be configured so as to display an alert icon image that is to be displayed on the training monitor 138. Further, examples of the setting parameters unrelated to the level of difficulty include parameters for increasing the degree of concentration of the trainee 900 on the training, such as the size and the displaying interval of the above-described alert icon image. Further, time information such as date and time at which the setting operation is performed or timing information other than the time (e.g., information indicating a distinction between the stance phase, the swing phase, etc. in one walking cycle) can be added to the above-described setting parameters.

The above-described item (2) is described.

The detection data of the above-described item (2) can be defined as training data of the trainee 900 that is acquired during the rehabilitation in the walking training apparatus 100 together with the data of the above-described item (1).

A typical example of the detection data is sensor data. The sensor data is sensor values detected by various sensors of the walking training apparatus 100. For example, the sensor data includes an inclination angle of the trunk detected by the posture sensor 217, a load and an inclination angle detected by the handrail sensor 218, an angle detected by the angle sensor 223, etc. The sensors that output the sensor data are an acceleration sensor, an angular-velocity sensor, a position sensor, an optical sensor, a torque sensor, a weight sensor, etc. Further, encoders provided in motors of the winding mechanisms or the like of the front wire 134, the rear wire 136, and the harness wire 111 may be used as sensors. Further, a torque sensor (a load cell) of the motor may be used as a sensor, or a current detection unit that detects a driving current value for driving the motor may be used as a sensor.

Further, the sensor data may include, for example, line-of-sight data acquired by a line-of-sight detection sensor that detects a line of sight. Similar line-of-sight data can be obtained by detecting a line of sight of the trainee 900 by performing image processing based on an image taken by shooting at least an area including the eyes of the trainee 900, or obtained by determining the orientation (upward/ downward etc.) of the face of the trainee 900 based on an image taken by shooting at least the face. Such data may also be included in the aforementioned detection data. Further, the detection data may be audio data (voice data) acquired by a voice acquisition unit, such as a microphone, that acquires a voice of the trainee 900 or the training staff member 901, text data obtained by performing a voice analysis on the voice data, or data obtained by analyzing the text data. The voice of the training staff member 901 may include an encouraging talk to the trainee 900 about, for example, how to correct his/her walking. Further, the sensor data may be data obtained by detecting brain waves of the trainee 900 by using an electroencephalograph, or may be data obtained by detecting brain waves of the training staff member 901 by using an electroencephalograph.

Further, the line-of-sight detection sensor, a shooting unit that takes the above-described image, a microphone, and the like can be disposed in the walking training apparatus 100 itself. Alternatively, they can also be disposed in, for example, an eyeglass-type wearable terminal that is worn by the trainee 900. This terminal may include a wireless communication unit that wirelessly transmits and receives data by a wireless communication technique such as Bluetooth (Registered Trademark). Further, the walking training apparatus 100 may also include a wireless communication unit. In this way, the walking training apparatus 100 can acquire data acquired by the wearable terminal through wireless communication. Although the electroencephalograph is limited to those having high detection accuracy, it may be disposed in the walking training apparatus 100 itself and configured so that the electroencephalogram of the trainee 900 and that of the training staff member 901 can be separately detected. However, the electroencephalograph may be disposed at a position near the person whose brain waves are detected, such as being disposed in the above-described eyeglass-type wearable terminal (e.g., in a side frame of the eyeglasses).

Further, the detection unit that acquires detection data, such as a sensor, is not limited to those described above with reference to FIGS. 1 to 3 or those exemplified by the eyeglass-type wearable terminal. For example, the trainee 900 may wear clothes equipped with a wearable biosensor and/or a wearable touch sensor. Here, the clothes are not limited to those worn on the upper body. That is, they may be those worn on the lower body, a top-and-bottom set, or those attached to a part of the harness 110 or the like. Further, a wireless communication unit like the one described above is provided in each of the clothes and the walking training apparatus 100. In this way, the walking training apparatus 100 can acquire data acquired by the wearable biological sensor or the wearable touch sensor through wireless communication. The wearable biosensor can acquire vital data such as the heart rate of the wearer. The wearable touch sensor can acquire data indicating information about a touch on the trainee 900, who is the wearer, made from the outside. That is, the wearable touch sensor can acquire data indicating information about a position where the training staff member 901 touched the trainee 900.

Further, the detection data is not limited to the values indicated by the detection signals detected by various sensors and the like. That is, they may include values calculated based on the detection signals from a plurality of sensors and statistical values obtained by statistically processing detection signals from one or a plurality of sensors or the like. As the statistical values, various statistical values such as an average value, a maximum value, a minimum value, and a standard deviation value may be used. Alternatively, they may be static statistical values or dynamic statistical values over a certain period such as one day, one training practice, or one walking cycle.

For example, the sensor data may include an open angle of the knee joint calculated from the angle between the upper-leg frame 122 and the lower-leg frame 123 detected by the angle sensor 223. Further, the sensor data of the angle sensor may include an angular velocity that is obtained by differentiate the angle. The sensor data of the acceleration sensor may be a velocity that is obtained by integrating the acceleration or a position that is obtained by integrating the acceleration twice.

For example, the detection data may include the below-described average value, the sum total value, the maximum value, the minimum value, and the representative value for each day or for each rehabilitation session on one day. Here, examples of the average value include an average speed (total walking distance/total walking time) [km/h], an average value of a stride length [cm], a walking rate [steps/min] indicating the number of steps per minute, a walking PCI [beats/m], and a falling-down prevention assistance [%]. The average speed may be, for example, a value calculated from a speed setting value of the treadmill 131 or a value calculated from the drive signal in the treadmill drive unit 211. The stride length means a distance from where one heel touches the ground to where the same heel touches the ground again. The PCI means a Physiological Cost Index (a clinical indicator of a physiological cost index). The walking PCI indicates energy efficiency during the walking. The falling-down prevention assistance [%] means a rate corresponding to the number of times of falling-down prevention assistance [times] per step, i.e., the number of times the training staff member 901 has assisted the trainee 900 to prevent him/her from falling down per step. That is, the falling-down prevention assistance [%] means a rate at which falling-down prevention assistance actions are performed for each step.

Further, examples of the sum total value include a walking time [s], a walking distance [m], the number of steps [steps], the number of times of falling-down prevention assistance [times], and a falling-down prevention assistance part and the number of times for each part [times].

Further, examples of the maximum value or the minimum value include maximum values or minimum values of a continuous walking time [s], a continuous walking distance [m], the number of continuous steps [steps], and a minimum value of a walking PCI [beats/m] (in other words, a longest distance the trainee can walk per beat). Examples of the representative value include a speed of the treadmill 131 that has been used most frequently (a representative speed [km/h]).

As described above, data supplied directly or indirectly from the detection unit such as various sensors can be included in the detection data. Further, time information such as date and time at which the detection is performed or timing information other than the time can be added to the above-described detection data.

Note that the above-described detection data is merely an example and other detection data may be used. Further, some of the above-described detection data may not be used. That is, when the detection data is used as rehabilitation data, the server 500 needs to collect at least one detection data.

The above-described item (3) is described.

The data related to the trainee 900 (hereinafter referred to as trainee data) indicates, for example, a property of the trainee 900. Examples of the trainee data include an age, a gender, a physique (a height, a weight, etc.) of the trainee 900, information about a symptom, a Br. Stage, an SIAS, an initial walking FIM, and a latest walking FIM. Further, the trainee data may also include a name or an ID of the trainee 900. Further, the trainee data may also include preference information indicating a preference of the trainee 900 and personality information indicating his/her personality. Further, the trainee data may include, as the FIM, an exercise item other than those related to the walking ability, and may include a recognition item. That is, the trainee data may include various data indicating physical abilities of the trainee 900. Note that part or all of the trainee data may be referred to as body information, basic information, or trainee feature information.

Note that the symptom information may include information indicating an initial symptom, a time when the symptom appears, and a current symptom. Further, it can be considered that the trainee 900 needs to perform rehabilitation mainly because of at least one of the symptoms described above. However, symptoms that are unlikely to be directly related to the rehabilitation may also be included in the symptom information. Further, the symptom information may also include a type(s) of a disease(s) (a name(s) of a disease(s) or a disorder(s)) that the subject has suffered from, such as a stroke (a cerebrovascular disorder) and a spinal cord injury. Further, the symptom information may also include, depending on the type of the disease, its classification. For example, strokes can be classified into cerebral infarction, intracranial hemorrhage (cerebral hemorrhage/subarachnoid hemorrhage), etc.

The Br. Stage means a Brunnstrom Recovery Stage in which a recovery process of a hemiplegia is divided into six stages based on the observation. The trainee data may include, of the Br. Stage, lower-limb items that are main items related to the walking training apparatus 100. The SIAS means a Stroke Impairment Assessment Set, which is an index for comprehensively evaluating dysfunction caused by a stroke. The SIAS may include a hip flexion test (Hip-Flex), a knee extension test (Knee-Ext), and a foot-pat test (Foot-Pat). Further, the SIAS may also include a lower limb tactile sensation (Touch L/E), a lower limb position sensation (Position L/E), an abdominal muscle strength (Abdominal), and a verticality test (Verticality).

The FIM (Functional Independence Measure) is one of the evaluation methods for evaluating ADL (Activities of Daily Life). In the FIM, a patient is evaluated (i.e., classified) into seven stages, i.e., one point to seven points according to the level of assistance.

For example, a walking FIM is a general index indicating the degree of recovery. A patient who can walk 50 m or longer without an assistant and without a harness (an assisting device) receives the highest score of seven points. Further, a patient who can walk less than 15 m no matter how much assistance is provided by one assistant receives the lowest score of one point. Further, when a patient can move 50 m with the minimum assistance (an assistance level of 25% or lower), he/she receives four points, whereas when a patient can move 50 m with medium assistance (an assistance level of 25% or higher), he/she receives three points. Therefore, as the recovery progresses, the walking FIM of the trainee 900 gradually increases. Note that the walking distance in the evaluation of the walking FIM is not limited to 50 m. For example, the walking distance may be 15 m.

As can be understood from the above description, the latest walking FIM used by the walking training apparatus 100 is used as not only an index indicating the physical ability of the trainee 900 but also an index indicating the degree of recovery of the trainee 900 from the start of the rehabilitation. The walking FIM is used as an index indicating the moving ability of the trainee 900 when no actuator is used, i.e., an index indicating his/her walking ability. In other words, the walking FIM is an important index in order to recognize the progress of the rehabilitation of the trainee 900. Further, the amount of change from the initial walking FIM to the latest walking FIM or its changing speed is also used as an index indicating the degree of recovery. The change speed may also be referred to as FIM efficiency. For example, the changing speed may be a value that is obtained by dividing the gain (the amount of change) up to the current FIM by, for example, the number of days of the rehabilitation, the number of elapsed days indicating a period of the rehabilitation, or the number of days the patient has been hospitalized in the case where the trainee 900 is a hospitalized patient.

Further, the walking FIM can be regarded as a score that is obtained under the condition at the time of the evaluation, such as when the patient wears the harness. In this case, information indicating the condition applied at the time of the evaluation may be added in the information indicating the walking FIM. The condition may include a condition at the time when the information is acquired, such as a wedge thickness, a used harness (e.g., with the walking assistance apparatus 120, with other walking assistance apparatuses, without any harness, etc.), a setting such as an angular setting of a part of the knee or the ankle in the harness, and/or whether the walking is performed on a level ground or on a slope. Further, in general, the walking FIM means a walking FIM in walking on a level ground. Further, level-ground walking information indicating such walking FIM may include information such as the longest distance that the patient has walked (the maximum continuous walking distance [m]) in the evaluation of the level-ground walking.

As described above, the trainee data in the above-described item (3) may include index data about rehabilitation performed by the trainee 900 by using the walking training apparatus 100, including at least one of the symptom, the physical ability, and the degree of recovery of the trainee 900. Note that in general, data that can be included in both concepts of the physical ability and the degree of recovery, such as the latest walking FIM, may be included in one of them. However, such data can also be included in both of them. Note that the same applies to all the items of the rehabilitation data. Further, data of a given item can be handled as data of one or a plurality of the above-described items (1) to (4). Further, time information such as the date and time at which the walking FIM is acquired, e.g., the measurement date of the walking FIM may be added in the above-described trainee data.

The above-described item (4) is described.

The data about the training staff member 901 (hereinafter referred to as staff data) indicates, for example, a property of the training staff member 901. The staff data includes a name or an ID, an age, a gender, a physique (a height, a weight, etc.) of the training staff member 901, a name of a hospital to which the training staff member 901 belongs, and his/her years of experience as a PT or a doctor. The staff data may include, as data related to the assistance, a value that numerically represents the timing at which the trainee 900 is assisted.

Further, in the case where a plurality of training staff members simultaneously assist the rehabilitation, the rehabilitation data may include data of the plurality of staff members. Further, each staff data may include information indicating whether the staff member is the main training staff member or an assistance training staff member. In addition to or instead of such information, each staff data may include information indicating whether the staff member is a training staff member who performs a setting operation and/or image checking in the management monitor 139, or whether or not the staff member is a training staff member who just physically supports the trainee 900 by hand.

Further, the walking training apparatus 100 may be configured so that a user (e.g., a training staff member) can enter a rehabilitation plan for the trainee 900. Further, the data of the rehabilitation plan entered as described above may also be included as staff data related to the training staff member 901 who has entered the data or as rehabilitation data belonging to other categories. Further, the walking training apparatus 100 may be configured so that, to make it possible to cope with the change of the training staff member 901, a user can enter remarks and/or messages for assisting the training of the trainee 900 in the future. Further, the data entered as described above may also be included as staff data related to the training staff member 901 who has entered the data or as rehabilitation data belonging to other categories.

The reason for including these data in the rehabilitation data is that there are possible situations where a training staff member has been able to successfully carry out the training of the trainee 900 because of the presence of remarks and/or messages given by other skilled training staff members. Further, time information such as the date and time at which the rehabilitation plan is entered, e.g., the input date and time of the rehabilitation plan may be added in the above-described staff data.

(Learning Stage)

Figure 5:
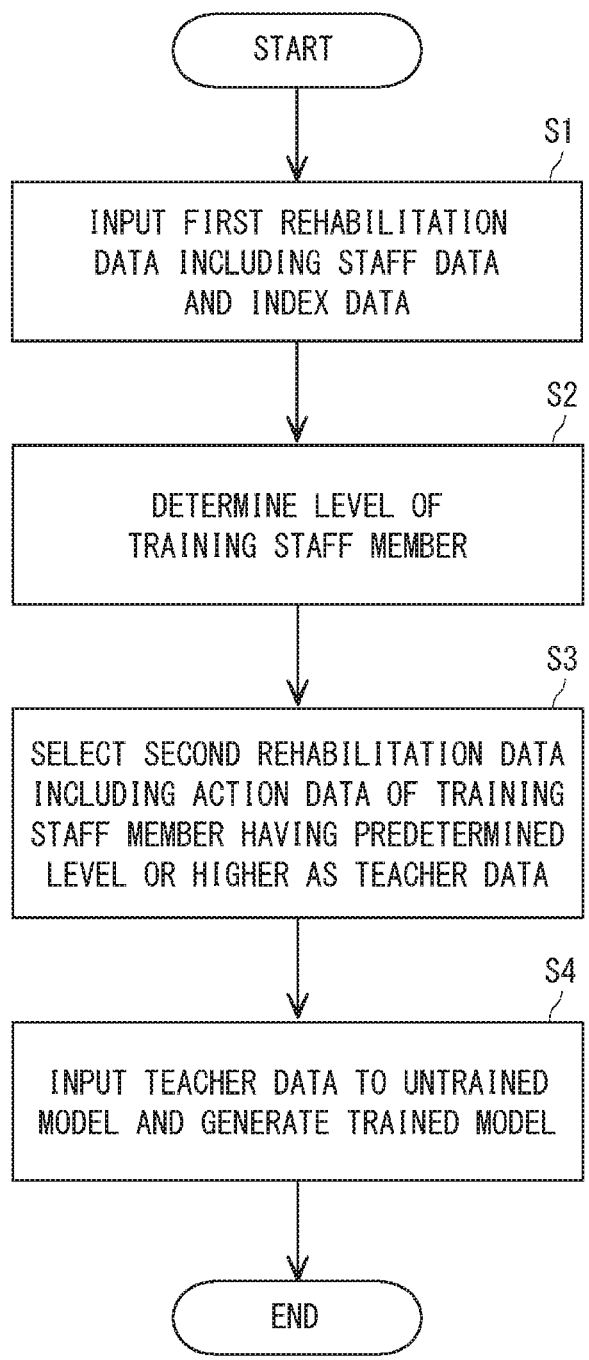
FIG. 5 is a flowchart for explaining an example of learning processes performed in the server shown in FIG. 4.

Next, processes performed in the learning stage (the learning phase) in the control unit 510 of the server 500 will be described with reference to FIG. 5. FIG. 5 is a flowchart for explaining an example of the learning process performed in the server 500.

The control unit 510 constructs a trained model from an untrained model by performing pre-processing (preliminary processing) on part or all of the information included in rehabilitation data like the one described above and performing machine learning by using the pre-processed data. The level determination unit 510a performs the pre-processing (the preparation processing) and the learning unit 510b performs the machine learning. However, the control unit 510 may also be configured so as to perform pre-processing other than the processing in the level determination unit 510a at the same time.

Firstly, the control unit 510 of the server 500 prepares a plurality of sets of data for the learning (in actuality, for the pre-processing thereof). Therefore, the control unit 510 prepares, for example, first rehabilitation data collected within a predetermined period as one set of learning data. For example, first rehabilitation data collected in one walking training session or one practice of walking training may be prepared as one set of learning data. Note that in the following description, one set of learning data is also referred to as a data set. The first rehabilitation data is data about rehabilitation that is performed by the trainee 900 by using the walking training apparatus 100 while being assisted by the training staff member 901 as required.

Note that one walking training session is a series of trainings performed by one trainee 900. Further, after one walking training session is completed by the trainee 900, the next trainee 900 performs training in the same walking training apparatus 100. One walking training session usually takes about 20 to 60 minutes. One practice of walking training is one unit during which the trainee 900 continuously walks, included in one walking training session. One walking training session includes a plurality of walking training practices. For example, one practice takes about five minutes. Specifically, in one walking training session, the trainee 900 takes a five-minute break after every time he/she performs walking training for five minutes. That is, a walking training practice and a break are alternately repeated in one walking training session. The five-minute interval between breaks is the time for one practice. Needless to say, neither of the time for one training session and the time for one practice is limited to any particular time period. That is, they may be set as appropriate for each trainee 900.

Further, the control unit 510 may prepare first rehabilitation data collected in a period shorter than the period of one practice as the learning data, or may prepare rehabilitation data collected in a period longer than the period of one practice as one set of learning data.

Then, the level determination unit 510a inputs the first rehabilitation data prepared as described above (step S1). Next, the level determination unit 510a determines a level indicating the evaluation (e.g., a degree of completeness) of the training staff member based on the input first rehabilitation data (step S2). The level determination unit 510a can be regarded as a selection unit that selects a training staff member(s) (e.g., a competent training staff member(s)).

The level determination unit 510a is an example of an output unit (a degree output unit) that outputs a degree (i.e., a level) indicating the evaluation of the training staff member, and a result of a determination made by the level determination unit 510a is an example of a result output from the degree output unit. That is, the level may be an example of the degree. Further, although they are not specifically described, levels related to other values may also be examples of the degrees. The degree output unit will be described hereinafter by using the level determination unit 510a as an example. However, the degree output unit may be a part that calculates and outputs an index value based on the evaluation of the training staff member as an example of the degree. For example, the level determination unit 510a may determine a level indicating the evaluation of the training staff member based on such an index value and output the determined level.

The above-described first rehabilitation data may be part or all of the above-described rehabilitation data and includes at least part of the staff data and part of the index data. In other words, the first rehabilitation data corresponds to rehabilitation data including at least staff data and index data that are used in the pre-processing stage (the level determination stage) of the learning.

As described above, the staff data is data indicating the training staff member 901 who assists the trainee 900, and may include, for example, a name or an ID of the training staff member 901 and a name of a hospital to which the training staff member 901 belongs. In particular, the staff data used here may include a name or an ID for identifying the training staff member 901. As described above, the index data is data indicating the degree of recovery of the trainee 900, and may include, for example, FIM efficiency of a walking FIM.

The level determination unit 510a can make a determination in accordance with a predetermined determination criterion. The predetermined determination criterion may be one or more of the following conditions (a) to (d) in terms of, for example, FIM efficiency, a walking speed, and stability of walking. However, the determination criterion is not limited to this example. The simplest example is years of experience. Note that the FIM efficiency is an example of a value indicating the recovery speed of the trainee.

(a) The average value or maximum value of the FIM efficiency (e.g., the length of a period before the FIM reaches six points or higher, or the length of a period before the patient can walk without assistance) for all the trainees assisted by the training staff member of interest is equal to or lower than a threshold.

(b) The average value or minimum value of the walking speed for all the trainees assisted by the training staff member of interest is equal to or higher than a threshold. Alternatively, the rate of increase of the walking speed is equal to or higher than a threshold.

(c) The average value or maximum value of the frequency of occurrences of abnormal walking in level-ground walking (walking on the treadmill 131) for all the trainees assisted by the training staff member of interest is equal to or lower than a threshold. Alternatively, the rate of decrease in the frequency is equal to or higher than a threshold.

(d) The indicator of the beauty of the walking for all the trainees assisted by the training staff member of interest is equal to or higher than a threshold. Note that an index indicating the beauty of the walking is included in the first rehabilitation data. Alternatively, the rate of increase of this index is equal to or greater than a threshold.

For each of the above-described items (a) to (d), a threshold set consisting of m−1 thresholds for m levels is prepared. Further, the threshold sets of the above-described items (a) to (d) are different from one another. Further, although data for all the trainees assisted by the training staff member of interest are processed by using thresholds in the above-described items (a) to (d), data for all the rehabilitation practices assisted by the training staff member of interest may also be processed by using thresholds. In this way, it is possible to take account of cases where two or more training staff members assist one trainee at the same time or in different periods.

Further, the process using thresholds can also be performed for rehabilitation data in which rehabilitation in which the training staff member takes part as the main staff member is distinguished from rehabilitation in which the training staff member takes part as an assistance staff member. Similarly, the process using thresholds can also be performed for rehabilitation data in which rehabilitation in which the training staff member takes part as a staff member operating the management monitor 139 is distinguished from rehabilitation in which the training staff member takes part as a staff member assisting the trainee (supporting the trainee by hand).

As a simple example, the level determination unit 510*a* may define that the number of levels in each of the above-described item (a) to (d) is two and determine whether or not the training staff member is a competent training staff member through the process using thresholds. Then, the level determination unit 510*a* may determine that the training staff member is competent (i.e., at a predetermined level or higher) when he/she is determined to be competent for at least three conditions. Further, in a simpler example, the level determination unit 510*a* uses only the above-described condition (a) as the condition and defines that the number of level is two. Then, the level determination unit 510*a* may determine a competent staff member, i.e., determine whether or not the training staff member is competent by performing a process using one threshold.

For the above-described determinations, basically, it is necessary to distinguish between training staff members. Therefore, in order to distinguish between training staff members, a name or an ID may be included in the staff data as described above. Note that even when such information is not included in the staff data, it is possible to roughly distinguish training staff members based on other information such as years of experience and an age.

In particular, the level determination unit 510*a* may determine the above-described level for each feature of the trainee 900. Note that in this case, it is assumed that the first rehabilitation data and the second rehabilitation data (which will be described later) include trainee data indicating features of the trainee 900. Examples of the features of the trainee 900 include a height, a weight, a gender, a disease, and a symptom. In this way, the level determination unit 510*a* can classify (i.e., select), for each gender of the trainees 900, training staff members who are considered to be competent for trainees having that gender.

In particular, the trainee data may include symptom data indicating at least one of a disorder (a name of a disease or a disorder) and a symptom of the trainee 900. This is because it is expected that the training staff member may be good at assisting for some diseases and symptoms of the trainee 900, but weak at assisting for other diseases and symptoms thereof. The symptom data is data in which the above-described symptom information is described. In particular, in the case of walking training, examples of symptoms that are included in the symptom data include a trunk backward movement, a trunk forward bending, a trunk diseased-side movement, a knee joint flexion, difficulty of the toe-off, difficulty in keeping the swinging leg, a trunk backward bending, a pelvic retreat, a lower leg forward bending, a knee joint extension, a flexed knee joint, and swinging. Further, examples of the symptoms that are included in the symptom data include a trunk normal-side movement, vaulting, pelvic elevation, hip joint external rotation, circumduction, and a medial whip. In this way, the level determination unit 510*a* can classify (i.e., select), for each disease or symptom of the trainees 900, training staff members who are considered to be competent for trainees having that disease of symptom.

Further, the level determination unit 510*a* may be configured so as to determine the above-described level for each value indicated by index data such as an initial FIM of the trainee 900. In this way, the level determination unit 510*a* can classify (i.e., select), for each value indicated by the index data of the trainees, training staff members who are considered to be competent for trainees having that value.

As a result of the determination by the level determination unit 510*a*, the learning unit 510*b* generates (constructs) a trained model by using, as teacher data, the second rehabilitation data corresponding to the training staff members determined to be at the predetermined level or higher (i.e., training staff members who are at a certain level or higher). The second rehabilitation data should include at least action data indicating an assisting action that is performed by the training staff member to assist the trainee. The trained model generated by the learning unit 510*b* is a model that inputs the above-described second rehabilitation data and outputs action data for suggesting the next action (the next assisting action) of the training staff member. The generation of such a trained model will be described.

Note that the type of the untrained model to be trained by the learning unit 510*b* and its algorithm are not limited to any particular types and algorithms. However, a neural network can be used as the algorithm and, in particular, a deep neural network (DNN) using multiple hidden layers may be used. As the DNN, for example, a feedforward (forward propagation type) neural network such as a multilayer perceptron (MLP) employing an error back propagation method can be used. Note that as described above, a publicly-known algorism can be used for the learning method used by the learning unit 510b (the same applies to the learning method used by a learning unit described in a third embodiment), and it is briefly described hereinafter while omitting detailed description thereof.

Examples of input parameters input to the untrained model in the learning unit 510b and output parameters output from the untrained model will be described hereinafter by using an example in which the learning unit 510b generates a trained model by using the MLP. Each of the input parameters corresponds to a respective one of nodes in the input layer and each of the output parameters corresponds to a respective one of nodes in the output layer (i.e., objective variables). Note that as described above, the untrained model includes not only a completely untrained model but also a model under a learning process. Further, the trained model indicates a model that can be used for an actual operation.

As described above, the second rehabilitation data includes at least action data. That is, the input parameters input to the untrained model include some or all of the above-described items of the action data. Note that the items of the action data indicate items indicating assisting actions. The items of the action data may be, for example, information indicating any of various types of assisting actions, such as an operation for setting a certain value to a certain setting parameter, an operation for setting another certain value to the setting parameter, an operation for supporting the trainee's waist by hand, and an operation for supporting the trainee's shoulder by hand.

Since the untrained model and the trained model are models for outputting action data, the output parameters also include some or all of the items of the action data. Further, since the number of input parameters to the untrained model is at least two, the second rehabilitation data includes data of at least two items. Further, the same applies to the trained model. Needless to say, both the action data in the second rehabilitation data and the action data as the output parameters can include items each of which indicates a respective one of a plurality of types of assisting actions.

The action data will be described from the viewpoint of acquisition paths. The action data may include part of detection data of the above-described item (2) in the above-described rehabilitation data. For example, the action data may include data indicating information that the trainee has been touched by the training staff member from the outside. Further, the action data may also include a setting parameter of the above-described item (1) set in the walking training apparatus 100 by the training staff member, and data obtained by extracting an action of the training staff member from recorded data. Note that the setting parameters included in the action data may include setting parameters automatically set based on default values or the like. In particular, the action data may include setting parameters that are automatically set by inheriting those of the previous practice.

As described above, the learning unit 510b generates a trained model by using, as teacher data, the second rehabilitation data corresponding to the training staff member who is determined to be at a predetermined level or higher. Therefore, subsequent to the step S2, the learning unit 510b selects, as the teacher data, the second rehabilitation data in which the training staff member having the predetermined level or higher takes part (step S3).

Therefore, the level determination unit 510a or the learning unit 510b may be configured so as to automatically attach the same correct-answer label to the second rehabilitation data of the training staff member having the predetermined level or higher. Alternatively, the level determination unit 510a or the learning unit 510b may be configured so as to automatically attach, to the second rehabilitation data of the training staff member having the predetermined level or higher, a correct-answer label corresponding to that level. An example case where the second rehabilitation data of training staff members having, of ten levels, i.e., levels 1 to 10, a level 7 or higher is used as the teacher data will be described. In this case, for example, a value "1.0" may be assigned to the correct-answer label (the correct-answer variable) of the second rehabilitation data in which a training staff member(s) having the most excellent level, i.e., a level 10 takes part. Then, for example, values "0.9", "0.8" and "0.7" may be assigned to the correct-answer variables of the second rehabilitation data in which training staff members having levels 9, 8 and 7, respectively, take part. In this way, when the determined level is higher, the second rehabilitation data may be assigned a correct-answer variable having a value with which the second rehabilitation data becomes more contributable to the construction of the learning model (e.g., to changes of weighting factors or thresholds).

Note that the above description is given on the assumption that the second rehabilitation data of training staff members having levels lower than the predetermined level is not used for the learning. In this regard, it is possible to use the second rehabilitation data by assigning a label indicating an incorrect answer, such as setting a value "0" to the correct-answer variable for the output parameter serving as the correct answer. The use of the second rehabilitation data of the training staff member having a level lower than the predetermined level is considered to be the use of the second rehabilitation data as negative teacher data. Further, an incorrect-answer label corresponding to the level may be assigned under the same concept as that for the correct-answer label corresponding to the level. In the case of the above-described example, for example, values "0.4" and "0.1" may be assigned to the correct-answer variables of the output parameters serving as correct answers for the second rehabilitation data in which training staff members having levels 4 and 1, respectively, take part. Note that the correct-answer label and the like may be manually assigned.

Then, the learning unit 510b inputs (i.e., supplies) the selected teacher data to the untrained model and thereby generates a trained model (step S4). When a forward propagation neural network such as the MLP is used, the learning unit 510b can input a data set that is obtained at the start of the rehabilitation or at each time point during the rehabilitation as one data set. However, the learning unit 510b can input a data set that is statistically obtained over a predetermined time as one data set at predetermined intervals. Alternatively, the learning unit 510b can input, as one data set, a data set statistically obtained over a predetermined period that starts from each time point (a time period longer than a unit time) at each time point. Further, in any case, one data set may be a data set that is statistically obtained over a certain period, such as over one step or over one walking cycle. In this case, the data set may be input every time the aforementioned certain period starts.

When the learning unit 510b generates the trained model, it inputs each of a plurality of sets of teacher data to the untrained model an appropriate number of times. For example, the learning unit 510b generates a trained model by using some of the sets of teacher data (training data for leaning) and checks the accuracy of the generated trained model by using the remaining sets as test data. As a result of the checking, if the accuracy is satisfactory, it is implemented as it is. On the other hand, if the accuracy is poor, some process, such as changing the pre-processing or performing tuning, is performed and then the trained model is generated and evaluated again. Note that it is also possible to prepare both evaluation data for checking the accuracy and test data for testing the final accuracy in advance. Further, it is possible to generate, according to the item of the data set that is input when the trained model is generated, the trained model in which that item is taken into consideration.

Further, hyper parameters to be tuned are not limited to any particular parameters. Examples of the hyper parameters to be tuned include the number of layers of the neural network, the number of units (number of nodes) in each layer, the number of times of iterative learning using the same data set (number of epochs), and the number of input data to be passed to the model at a time (a batch size). Further, examples of the hyper parameters to be tuned include a learning coefficient and a type of an activation function. Note that the learning coefficient is also referred to as a learning rate and may be as a value for determining how much the weight of each layer is changed at a time.

Through the above-described processes, it is possible to construct a trained model that outputs action data indicating an assistance action to be suggested based on the current state. Further, each of the output parameters may be associated with an item to be suggested in the action data. In this way, as will be described later, the walking training apparatus 100 using the above-described trained model can use acquired data as an input parameter, output action data indicating an assistance action to be suggested, and thereby suggest the assistance action to the training staff member.

Further, the second rehabilitation data may include at least one of index data and staff data. In this way, it is possible to change what should be suggested according to the level of the training staff member or the value of the index data of the trainee (e.g., the FIM efficiency).

Further, the action data may include at least one of assistance performance data and setting operation data. The assistance performance data is data indicating an assisting action for the trainee and can be data that is obtained by detecting, from a sensor or image processing or the like, that the training staff member has assisted the trainee with bare hands or the like.

Further, the setting operation data is data indicating an operation by which a setting value in the walking training apparatus 100 is changed, i.e., is data indicating the method for using the setting value. The setting operation data can include data indicating the level of proficiency (the level of proficiency related to the setting operation), such as a time required from when a setting window is opened on the management monitor 139 to when its setting operation or all the setting operations are completed. This is because it is possible to infer, to some extent, whether or not the training staff member has a lot of experience based on the level of proficiency. Note that the operation reception unit 212 cannot determine whether the operation is performed by the training staff member 901 or by the trainee 900. However, in the case of rehabilitation in which the training staff member 901 is designated, the operation may be processed while presuming that it has been performed by the training staff member 901. Needless to say, it may be configured so as to determine whether the operator is the training staff member 901 or the trainee 900 based on the image data taken by the camera 140.

As can be understood from the above examples, the items included in the second rehabilitation data can be the same as those included in the first rehabilitation data. However, for example, some items such as the name or the ID of the training staff member included in the first rehabilitation data may be excluded from the second rehabilitation data.

Next, examples of other kinds of learning models will be shown. Some of the second rehabilitation data may be input as image data to a feature extraction unit including, for example, a convolution layer and a pooling layer in a CNN (Convolutional Neural Network). Examples of the image data include image data representing a trajectory of the COP of ten steps. In such a case where the feature extraction unit is provided, a result of extraction of features from the image data may be input to all the connection layers in parallel with other input parameters.

Further, as the neural network, for example, a neural network having a recursive structure such as an RNN (Recurrent Neural Network) may be used. Further, the RNN may be a neural network that is extended to include an LSTM (Long Short-Term Memory) block (also referred to simply as an LSTM). In the case of using a recursive model having the RNN, for example, one data set may include time-series data such as detection data so that the learning unit 510b successively inputs second rehabilitation data at each time point in one practice. That is, one data set (one learning data set) may include time-series log data. Further, one data set may include feature values extracted from the log data as described above, or may include image data obtained by performing data processing on time-series detection data.

Further, when a recursive model having the RNN is used, for example, the learning unit 510b can input a data set statistically obtained over a predetermined time as one data set at predetermined intervals. Alternatively, even when a recursive model is used, the learning unit 510b can input, as one data set, a data set statistically obtained over a predetermined period that starts from each time point (a time period longer than a unit time) at each time point. Further, one data set may be a data set that is statistically obtained over a certain period, such as over one step or over one walking cycle. In this case, the data set may be input every time the aforementioned certain period starts. Note that the category of such statistical processing may include the above-described process for obtaining image data by performing data processing on time-series detection data.

In this way, it is possible to construct a trained model that timely outputs action data that is predicted from the past only through a period obtained from the period of one data set such as the above-described predetermined time and the number of stored steps based on the current state and a past state that is a little earlier than the current state and indicates an assisting action to be suggested at present. Then, as will be described later, the walking training apparatus 100 using the above-described trained model successively inputs data acquired during the rehabilitation as input parameters and can output action data indicating an assisting action that is predicted as ought to be suggested in a scene where a suggestion is required. That is, in the walking training apparatus 100, it is possible to suggest, to the training staff member, an assisting action that is predicted as ought to be suggested.

As can be understood from these examples, the items and/or the time ranges included in the above-described second rehabilitation data are usually changed according to the learning model used in the learning unit 510*b*.

Further, among the output parameters, m output parameters (m is a positive integer) may be, for example, m setting values that exist for each one of the setting parameters of the above-described item (1). Similarly, among the output parameters, l output parameters (l is a positive integer) may be, for example, l detection timings or detection positions that exist for each one of the detection data of the above-described item (2).

In these cases, the number of nodes in the output layer of the trained model is increased. Therefore, a plurality of trained models can be constructed. For example, a trained model is constructed for each setting parameter to be output or each detection data, or a trained model is constructed for each assistance position to be output. Further, by storing these trained models in the model storage unit 521, these trained models can be simultaneously operated.

Further, the above-described examples are described on the assumption that the level determination unit 510*a* is provided in the learning apparatus. However, the level determination unit 510*a* may not be provided in the learning apparatus. In such a case, the learning apparatus exemplified by the server 500 may include an acquisition unit that acquires a determination result that is obtained based on the first rehabilitation data and is a determination result of the determination of the level indicating the evaluation of the training staff member 901. This acquisition unit can be formed by, for example, the communication IF 514 and an acquisition control unit in the control unit (e.g., in the response processing unit 510*c*) that controls the communication IF 510. The acquisition unit may be configured so as to acquire a determination result from a level determination unit provided in an external apparatus such as a PC or the walking training apparatus 100. Alternatively, for example, a person may calculate the level by using spreadsheet application software based on the first rehabilitation data in a PC or the like. In this case, the acquisition unit may be configured so as to input the calculated result (the determination result) as input data.

Further, the above description has been given on the assumption that the learning unit 510*b* generates a trained model by using, as the teacher data, the second rehabilitation data corresponding to the training staff member who is determined to be at the predetermined level or higher. In this way, it is possible to generate a trained model in which the action performed by the training assistant at the predetermined level or higher is taken into consideration.

Alternatively, as alternative processing, it is also possible to make the training model learn regardless of whether or not the training assistant is at the predetermined level or higher. For example, the learning unit 510*b* can generate a learning model by using, as the teacher data, second rehabilitation data in which a plurality of levels that are labeled based on determination results are associated with staff data each of which corresponds to a respective one of the plurality of levels. The aforementioned process for the association corresponds to the pre-processing. The aforementioned plurality of levels may be a plurality of levels included in all the levels to be determined, or may be all the levels. By using such teacher data, it is possible to generate a trained model in which the action performed by the training staff member is taken into consideration on a level-by-level basis.

In other words, in the aforementioned alternative processing, the levels determined for the training staff members are individually labeled for each training staff member (i.e., for staff data). Next, the learning unit 510*b* learns the action data included in the second rehabilitation data while associating them with the labelled levels by using the second rehabilitation data (excluding the staff data) and the staff data, i.e., by using the second rehabilitation data including the staff data.

For example, the labelling is performed in such a manner that the more competent the training staff member is, the higher the level becomes. Further, the association of the learning is performed in such a manner that the higher the level of the label is, the higher the weight in the learning becomes. In a more specific example, as in the case where second rehabilitation data of a training staff member having a predetermined level or higher is used, it is possible to realize this feature by assigning correct-answer variables in such a manner that when the determined level is higher, the second rehabilitation data may be assigned a correct-answer variable having a value with which the second rehabilitation data becomes more contributable to the construction of the learning model (e.g., to changes of weighting factors or thresholds). However, in the aforementioned alternative processing, the used second rehabilitation data is not limited to the data of the training staff member having the predetermined level or higher. That is, the second rehabilitation data may be any data of a training staff member having a plurality of predetermined levels (e.g., having a plurality of successive levels).

As described above, the learning unit 510*b* generates a learning model by using, as teacher data, second rehabilitation data for which pre-processing has been performed based on a determination result as exemplified by the threshold processing using predetermined levels and the above-shown alternative processing. Note that the aforementioned pre-processing is not limited to the above-described threshold processing based on the predetermined levels and the associating processing on a level-by-level basis. For example, in the pre-processing, the determination result may be simply associated with the second rehabilitation data. In any case, it is possible to generate, when a trainee performs rehabilitation by using the walking training apparatus 100, a learning model capable of suggesting a desirable action to a training staff member who assists the trainee.

(Operation Stage)

Next, processes performed in the operation stage (the inference phase) in the walking training apparatus 100 and the server 500 will be described. As described above, the walking training apparatus 100 is configured so as to be able to access a trained model, so that it can use the trained model. Note that the trained model may also be referred to as a trained module. In the operation stage, in general, the walking training apparatus 100 and the server 500 connected thereto cooperate with each other. That is, they serve as a rehabilitation support system and perform a rehabilitation support process.

In order to operate (i.e., make use of) the above-described trained model, the walking training apparatus 100 may include an output unit and a notification unit as described below. The output unit outputs second rehabilitation data related to rehabilitation performed by a trainee by using the walking training apparatus 100 to the trained model as an input. Further, the output unit may be exemplified by the input/output control unit 210*c* and the input/output unit 231. The notification unit notifies a training staff member who assists the trainee in the rehabilitation of action data output from the trained model. Further, the notification unit may be exemplified mainly by the notification control unit 210*d*, the display control unit 213, and the management monitor 139 (or by an audio control unit and a speaker(s)).

Meanwhile, on the server 500 side, the response processing unit 510c operates the trained model stored in the model storage unit 521 and thereby performs a response process. Further, the server 500 include an input/output unit that inputs the second rehabilitation data output from the above-described output unit to the trained model and outputs an output from the trained model to the walking training apparatus 100. This input/output unit may be exemplified by the communication IF 514 or the like.

Figure 6:
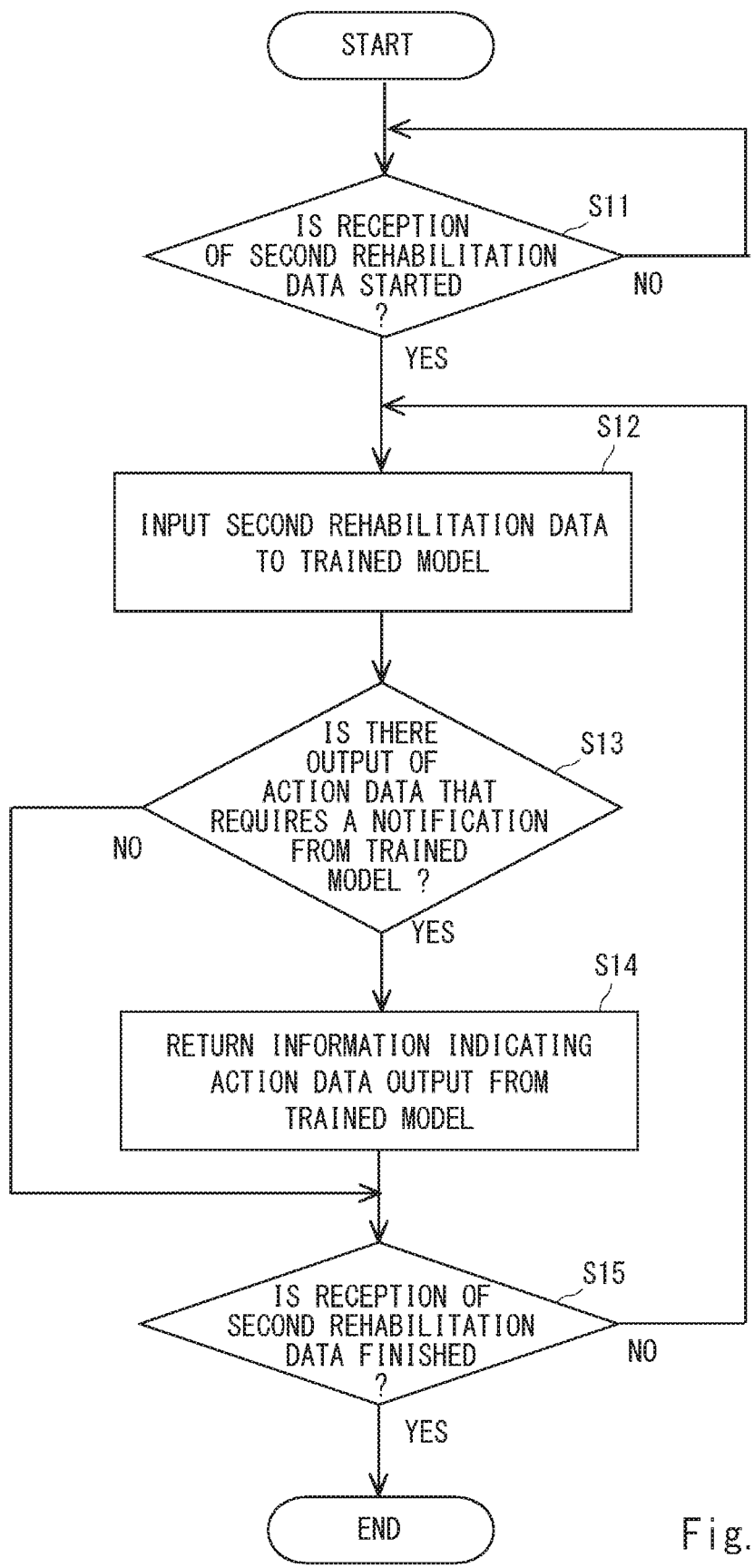
FIG. 6 is a flowchart for explaining an example of rehabilitation support processes performed in the server shown in FIG. 4.

An example of the rehabilitation support process in the rehabilitation system including the server 500 will be described in a concrete manner with reference to FIG. 6. FIG. 6 is a flowchart for explaining an example of the rehabilitation support process performed in the server 500.

Firstly, the input/output control unit 210c outputs acquired data (second rehabilitation data) that could be used as an input parameter to the server 500 through the input/output unit 231. The aforementioned acquired data may be data acquired at the start of the rehabilitation or data acquired at each time point during the rehabilitation.

When the response processing unit 510c of the server 500 receives this data through the communication IF 514 (Yes at step S11), it starts a response process. The response processing unit 510c analyzes the received data, divides them into a plurality of item data, and outputs each of the item data as a respective one of input parameters in an input layer in the trained model stored in the model storage unit 521 (step S12).

The response processing unit 510c performs calculation by operating the trained model, determines each output parameter from the output layer, and thereby determines whether or not there is an output of an item of action data (an item indicating an assisting action) that needs to be suggested to the training staff member (i.e., action data of which the training staff member needs to be notified) (step S13). Note that each of the output parameters corresponds to a respective one of the assisting actions of which the training staff member should be notified. Further, the determination of the output parameters can be made by performing a process by using thresholds each of which is prepared for a respective one of the values of the output parameters in advance (or by using a common threshold). Needless to say, in the case of a model whose output parameter can have only two values, i.e., values 0 and 1, all that has to be performed is to determine whether the output parameter is 0 or 1.

When the determination result at the step S13 is Yes, the response processing unit 510c returns the information that has been output as an output parameter from the trained model and indicates the action data of which the training staff member needs to be notified (the information of the item indicating assisting action) to the walking training apparatus 100 side through the communication IF 514 (step S14). The information to be returned may be a command to the walking training apparatus 100. If the determination result at the step S13 is No, the response processing unit 510c proceeds to a step S15 (which will be described later) without going through the step S14.

As described above, in the steps S13 and S14, the response processing unit 510c performs calculation while operating the trained model, and thereby generates a command corresponding to the output parameter output as a value of which the training staff member needs to be notified among the output parameters from the output layer. Meanwhile, the response processing unit 510c does not perform any particular process for the other output parameters. That is, in some cases, the response processing unit 510c does not output any command at all depending on the calculation result. Such cases correspond to situations where no suggestion (no notification) is necessary for the training staff member. Note that the command can be generated by, for example, reading a command corresponding to the output parameter from a group of commands stored in advance. Further, the command may simply indicate information indicating the output parameter (e.g., information indicating the ordinal position of the node in the output layer). The response processing unit 510c transmits the generated command to the walking training apparatus 100 side through the communication IF 514.

After the process in the step S14, the response processing unit 510c determines whether or not the reception of the second rehabilitation data has been completed (step S15). Then, when the reception has been completed, the response processing unit 510c finishes the process, whereas when the reception has not been completed, it determines that the rehabilitation is in progress and returns to the step S12.

In the walking training apparatus 100, the input/output control unit 210c receives the command transmitted in the step S14 and passes the received command to the notification control unit 210d. The notification control unit 210d performs notification control corresponding to this command for the display control unit 213 or an audio control unit (not shown). Notification controls each of which corresponds to a respective one of the commands in the command group that could be transmitted from the server 500 side may be stored in the notification control unit 210d in advance. The notification control unit 210d makes the display control unit 213 output, to the management monitor 139, a display control signal for displaying, for example, an image corresponding to the command on the management monitor 139. For example, the notification control unit 210d makes the aforementioned audio control unit output, to a speaker(s), an audio control signal for outputting a sound corresponding to the command from the speaker(s). Note that some suggestions such as a suggestion of assistance with bare hands may be given by displaying a still image or moving images for explaining an assisting method.

Through the above-described processes, in the walking training apparatus 100, it is possible to use acquired data as an input parameter, output action data indicating an assisting action to be suggested (an assisting action that was performed by a competent training staff member), and thereby suggest the assisting action to the training staff member. That is, in the walking training apparatus 100, through such a suggestion, it becomes possible to advise the training staff member on an assisting action (setting, assistance, etc.) that he/she should perform next. Further, since the trained model exists in the server 500, a plurality of walking training apparatuses 100 can be operated by using the common trained model.

In an example of use, for example, the walking training apparatus 100 may be configured so as to input a data set consisting of setting parameters that are set before the start of one rehabilitation session to the trained model and, as the need arises, make a suggestion on the setting parameters before the rehabilitation session is started. For example, the walking training apparatus 100 may be configured so as to use, as an input, a data set consisting of statistical values of data obtained during the rehabilitation having the aforementioned predetermined period or the aforementioned certain period and, as the need arises, suggest setting parameters or assistance with bare hands that is expected to be required.

The above-described examples have been explained on the assumption that an output and a notification are given to the training staff member at all the levels. This is because even a competent training staff member could forget to make some setting and it is necessary to prevent such omissions.

On the other hand, the walking training apparatus 100 may be configured so as to perform the process related to the notification only for training staff members 901 whose are not considered to be competent and for whom the notification is necessary. Specifically, firstly, the walking training apparatus 100 may include a designation unit that designates a training staff member 901 who assists the trainee in the rehabilitation by his/her name or ID. This designation unit may be exemplified by, for example, the management monitor 139 equipped with a touch sensor. Further, in addition to including the designation unit, the walking training apparatus 100 may be configured so as to be able to access to a level storage unit that stores a level determined by the level determination unit 510a. This level storage unit may be, for example, a storage device connected to the overall control unit 210 or the overall control unit 210, or may be a storage device disposed inside the server 500.

Further, in the walking training apparatus 100, when the training staff member 901 designated by the designation unit is not at a level equal to or higher than a predetermined level, the above-described output unit outputs second rehabilitation data and the above-described notification unit provides a notification. That is, in the walking training apparatus 100 in this example, when the training staff member 901 who is assisting the trainee 900 is a training staff member having the predetermined level or higher, no second rehabilitation data is output and hence no notification is provided. In this way, it is possible to prevent unnecessary notifications from being provided to training staff members who are assumed to require no notification.

The above example has been explained on the assumption that the process using thresholds is performed according to the predetermined level. However, the present disclosure is not limited to such examples. Even in the case of the above-described alternative processing, the walking training apparatus 100 may provide an output and a notification when the level of the training staff member 901 designated by the designation unit is a level that is used as that of teacher data in the trained model.

Figure 8:
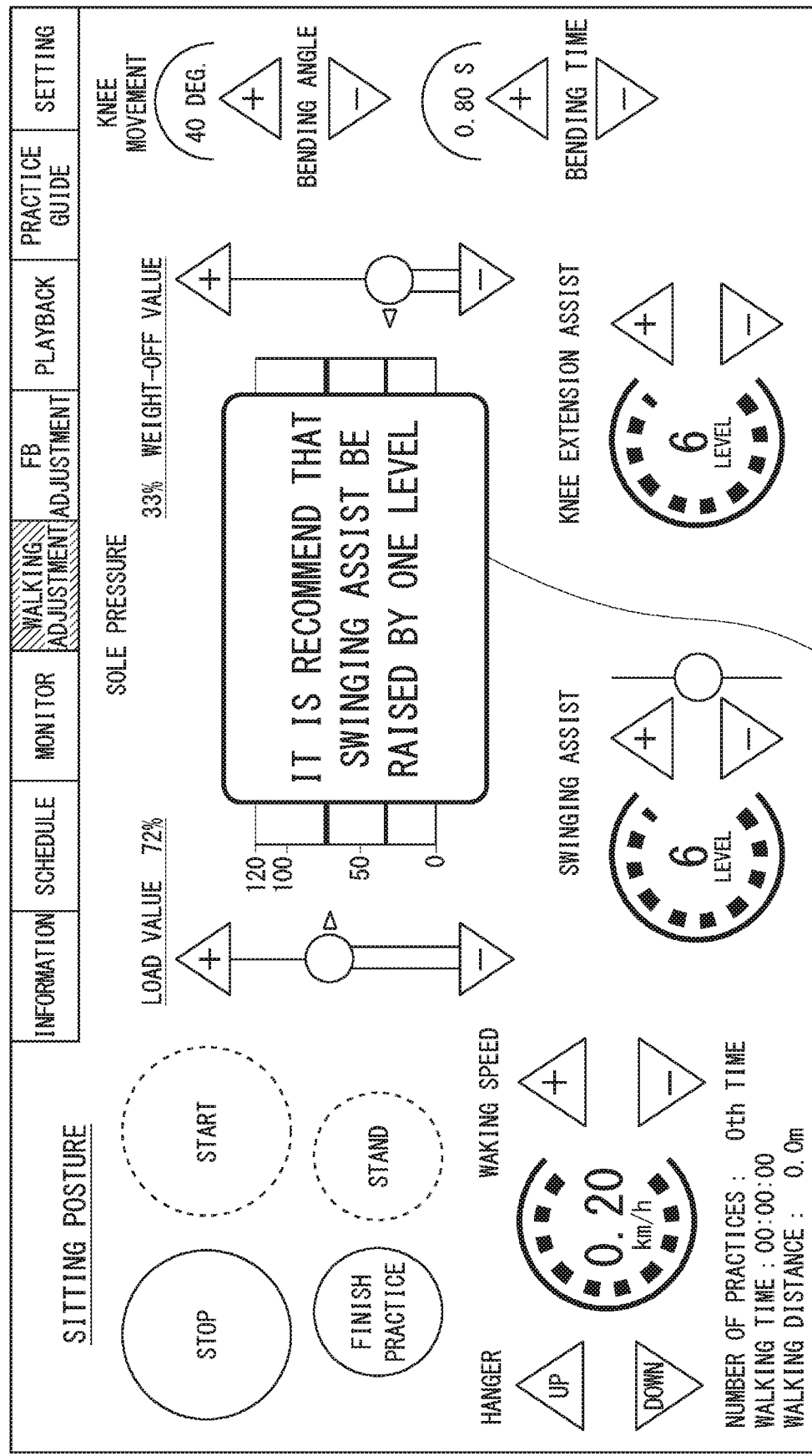
FIG. 8 shows an example of an image presented to a training staff member in the rehabilitation support process shown in FIG. 6.
Figure 9:
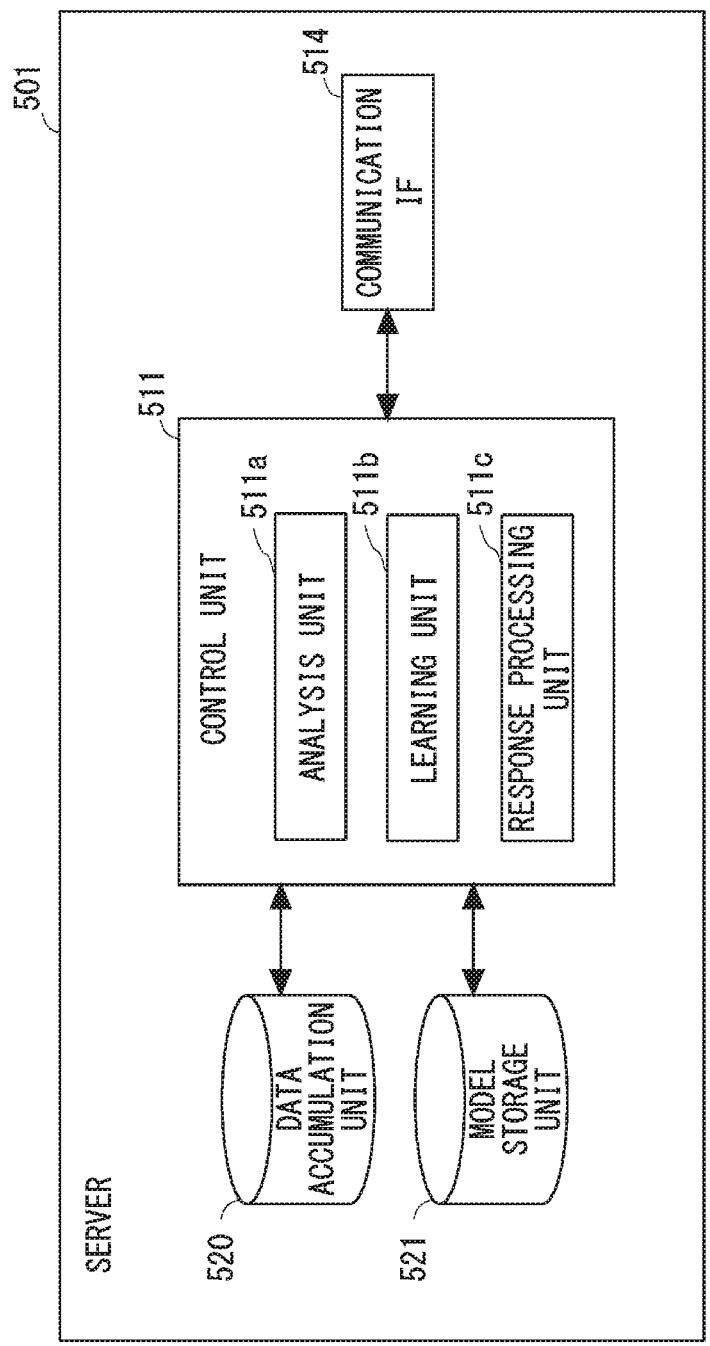
FIG. 9 is a block diagram showing an example of a configuration of a server in a rehabilitation support system according to a second embodiment.

Next, an example of a suggestion to the training staff member 901 in the above-described walking training apparatus 100 will be described with reference to FIGS. 7 and 8. FIG. 8 shows an example of an image that is shown to a training staff member in the rehabilitation support process shown in FIG. 7, and FIG. 9 shows another example of such an image.

Figure 7:
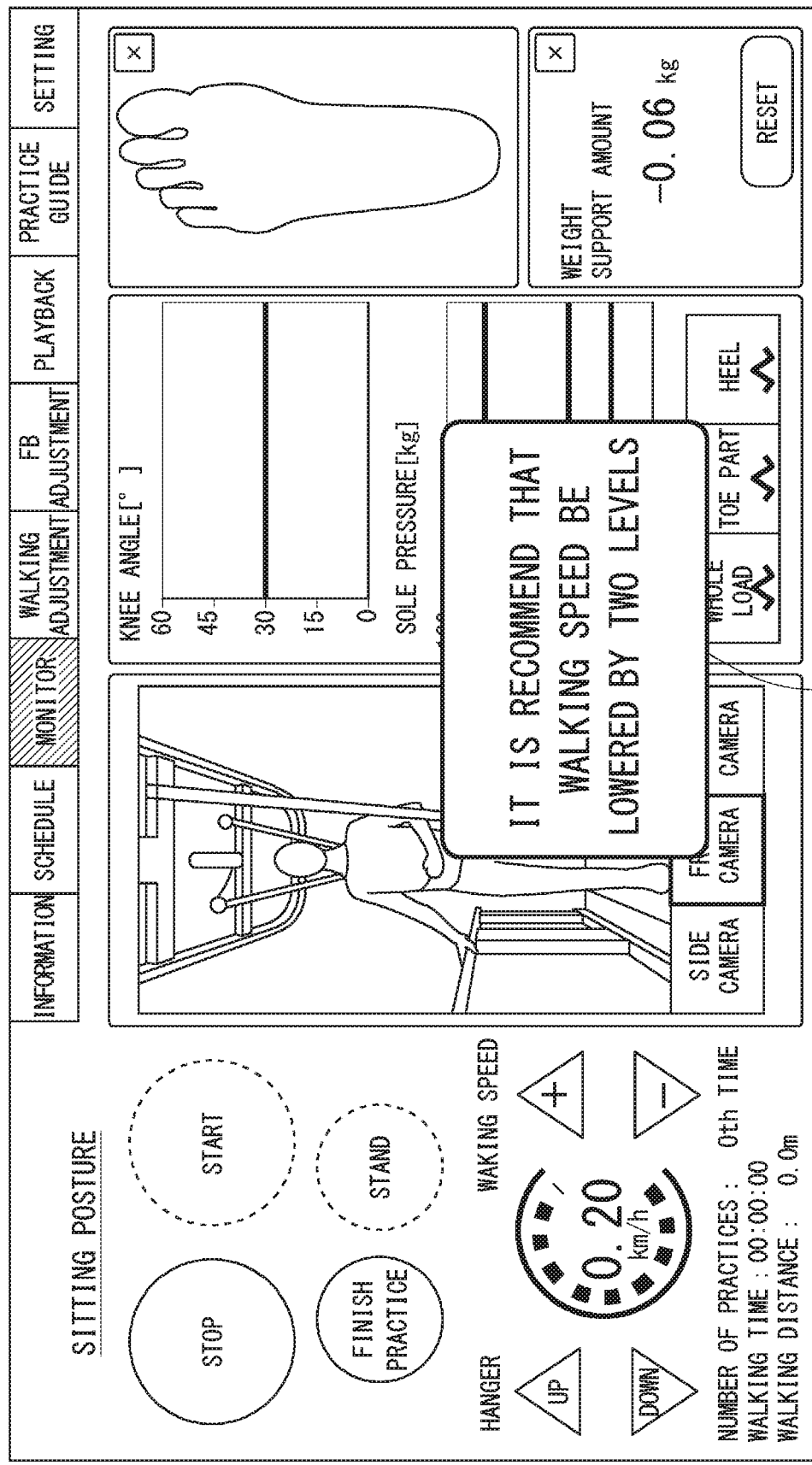
FIG. 7 shows an example of an image presented to a training staff member in the rehabilitation support process shown in FIG. 6.

In a GUI (Graphical User Interface) image 139a shown in FIG. 7, a pop-up image 139b is superimposed on an image displayed on the management monitor 139 during the rehabilitation. The pop-up image 139b is displayed when the walking training apparatus 100 receives, from the server 500, command suggesting that the walking speed be reduced by two levels. Note that the image on which the pop-up image 139b is superimposed is an image that is displayed at the time when a suggestion is given, and the content included in that image is not limited to any particular content.

In the GUI image 139c shown in FIG. 8, a pop-up image 139d is superimposed on an image displayed on the management monitor 139 during the rehabilitation. The pop-up image 139d is displayed when the walking training apparatus 100 receives, from the server 500, a command suggesting that the level of the swinging assist be increased by one level. Note that the image on which the pop-up image 139d is superimposed is an image that is displayed at the time when a suggestion is given, and the content included in that image is not limited to any particular content.

(Effect)

As described above, in the learning apparatus according to this embodiment, data for which a good training staff member(s) took part in the preparation processes are classified based on the level classification of the training staff members. Then, a trained model is generated by using the data for which the good training staff member(s) took part as an input. The generated trained model can be used as a model that outputs a good assisting action (a change in setting values including an assistance level, encouraging talks to the trainee, assistance with bare hands, etc.) as required, or as a model that outputs a good assisting action at a required timing. Therefore, according to this embodiment, it is possible to construct a trained model capable of outputting information indicating a good assisting action, i.e., capable of suggesting a desirable action to a training staff member.

Further, according to the walking training apparatus 100 in accordance with this embodiment, since it is possible to access the trained model generated as described above, it is possible to suggest a desirable action to a training staff member. Therefore, according to the above-described walking training apparatus 100, it is possible to give suggestions as if they are assisted by a competent training staff member regardless of the degree of competence of the actual training staff member that changes according to his/her years of experience, level of proficiency, ability, etc.

For example, in the case where a forward propagation type neural network is used for the learning model, it becomes possible to suggest an appropriate setting parameter and the like as a response to the second rehabilitation data transmitted to the server 500 side before the rehabilitation is started. Similarly, when the second rehabilitation data is transmitted to the server 500 side at regular intervals during the rehabilitation, it is possible to receive a suggestion that is necessary at that time. For example, when a neural network having a recursive structure is used for the learning model, such suggestions can be given in a predicted manner while taking slightly-earlier second rehabilitation data into consideration. The timing of the suggestion can also be appropriately adjusted by appropriately setting the statistical period and the number of stored steps of one data set. As described above, in the walking training apparatus 100 according to this embodiment, it is possible to suggest a change of a setting parameter, an encouraging talk to the trainee, assistance by bare hands for the trainee, and the like at appropriate timings.

(Supplemental Remarks on Method and Program)

As can be understood from the above-described description, in this embodiment, a learning method including the following acquisition step and learning step can also be provided. In the acquisition step, an output result obtained by outputting a degree such as a determination result obtained by determining a level indicating an evaluation of a training staff member is acquired based on first rehabilitation data. In the learning step, a learning model that inputs second rehabilitation data including at least action data indicating an assisting action performed by a training staff member to assist a trainee and outputs action data for suggesting the next action to be performed by a training staff member is generated. Further, in the learning step, a learning model is generated by using, as teacher data, second rehabilitation data for which pre-processing has been performed based on an output result such as a determination result.

In this embodiment, as can be understood from the above-described description, it is also possible to provide a method for supporting rehabilitation (a method for operating the walking training apparatus 100) in the walking training apparatus 100 capable of accessing a trained model, which is a learning model trained by the above-described learning method. Further, this method includes the below-shown outputting step and the notification step. In the outputting step, the walking training apparatus 100 outputs second rehabilitation data related to rehabilitation performed by a trainee by using the walking training apparatus 100 as an input to the trained model. In the notification step, the walking training apparatus 100 notifies a training staff member who is assisting the trainee in the rehabilitation of action data output from the trained model.

In this embodiment, as can be understood from the above-described description, it is also possible to provide a program (a learning program) for causing a computer to perform the above-described acquisition step and the learning step. Needless to say, it is also possible to provide a trained model trained by the learning apparatus, a trained model trained by the learning method, and a trained model trained by the learning program. Further, in this embodiment, as can be understood from the above-described description, it is also possible to provide a rehabilitation support program for causing a computer of the walking training apparatus 100 capable of accessing the above-described trained model to perform the above-described outputting step and notification step.

Second Embodiment

In the first embodiment, an example in which the server 500 includes the level determination unit 510*a* and the learning unit 510*b*, and the server 500 generates a trained model is shown. In contrast, in this embodiment, a degree output unit such as the level determination unit and the learning unit are provided on the walking training apparatus 100 side (e.g., in the overall control unit 210). A rehabilitation support system according to this embodiment may include the walking training apparatus 100. However, in this case, in order to increase the amount of rehabilitation data collected in the learning stage, the rehabilitation support system may be configured so that rehabilitation data from other walking training apparatuses can be collected.

Further, regarding the operation stage, an example in which the trained model is provided in the server 500, and the walking training apparatus 100 transmits rehabilitation data to the server 500 and receives action data from the server 500 has been described. However, the present disclosure is not limited to such examples. For example, a trained model may be incorporated on the walking training apparatus 100 side (e.g., in a storage unit in the overall control unit 210). For this purpose, the walking training apparatus 100 may include a storage unit that stores the trained model. Further, although it is not specifically described, the various examples described above in the first embodiment can also be applied to this embodiment and the same effects as those in the first embodiment can be achieved. For example, in this embodiment, an acquisition unit may also be provided in place of the level determination unit as in the first embodiment. That is, the walking training apparatus 100 according to this embodiment may include an acquisition unit in place of the degree output unit such as the level determination unit.

Third Embodiment

A third embodiment will be described with reference to FIGS. 9 to 11. FIG. 9 is a block diagram showing an example of a configuration of a server in a rehabilitation support system according to the third embodiment. Although the detailed description of the rehabilitation support system according to this embodiment is omitted, it may include a rehabilitation support apparatus such as the walking training apparatus 100 described in the first embodiment. Further, although it is not specifically described, the various examples described above in the first embodiment can also be applied to this embodiment, except for the following differences.

A learning apparatus according to this embodiment is different from the learning apparatus according to the first embodiment in that it includes the below-shown analysis unit in place of the degree output unit such as the determination unit exemplified by the level determination unit 510*a*. The learning apparatus according to this embodiment may be exemplified by the server 501 and the aforementioned analysis unit may be exemplified by the analysis unit 511*a*.

A server 501 shown in FIG. 9 may include a learning unit 511*b* and a response processing unit 511*c* which correspond to the learning unit 510*b* and the response processing unit 510*c*, respectively, of the server 500 shown in FIG. 4. The analysis unit 511*a*, the learning unit 511*b*, and the response processing unit 511*c* may be disposed in a control unit 511 corresponding to the control unit 510 shown in FIG. 4. Basically, the control unit 511 includes the analysis unit 511*a* in place of the level determination unit 510*a* provided in the control unit 510. In particular, the response processing unit 511*c* may basically perform the same process as that performed by the response processing unit 510*c*.

(Learning Stage)

Next, processes performed in the learning stage by the control unit 511 of the server 501 will be described with reference to FIGS. 10 and 11. FIG. 10 is a schematic diagram showing an example of a result of a cluster analysis performed by the server, and FIG. 11 is a flowchart for explaining an example of the learning process performed in the server 501.

The control unit 511 performs pre-processing on part or all of the information included in the rehabilitation data, performs machine learning using the pre-processed data, and thereby constructs a trained model from an untrained model. The analysis unit 511*a* performs the pre-processing (the preparation processing) and the learning unit 511*b* performs the machine learning. However, the control unit 511 may also be configured so as to perform pre-processing other than the processing in the analysis unit 511*a* at the same time.

Firstly, the analysis unit 511*a* inputs first rehabilitation data (step S21). The first rehabilitation data includes at least staff data that indicates a training staff member 901 who assists a trainee 900 for rehabilitation performed by the trainee 900 by using the walking training apparatus 100. Further, the first rehabilitation data also includes at least action data indicating an assisting action performed by the training staff member 901 to assist the trainee 900, and index data indicating the degree of recovery of the trainee 900. In particular, it is appropriate to determine whether or not the training staff member is competent, i.e., whether or not the first rehabilitation data is one for which a competent training staff member took part based on the recovery index of the trainee. Therefore, the index data is particularly important.

The analysis unit 511a classifies the training staff members by performing a cluster analysis on the above-described first rehabilitation data (step S22). For the cluster analysis performed by the analysis unit 511a, for example, a k-means method can be used. Although the clusters, which are a result of the analysis, become those into which the tendency of the first rehabilitation data is classified, they may be adjusted so that they correspond to respective data groups that are classified according to the level of the competence of the training staff members.

For the cluster analysis performed by the analysis unit 511a, an X-means method in which the k-means method is extended and the number of clusters is automatically specified may be used. Further, for the cluster analysis performed by the analysis unit 511a, other various methods such as Gaussian Mixture Models (GMMs) capable of obtaining a probability density distribution and spectral clustering in which clustering is performed while paying attention to connectivity can be used. Note that in the spectral clustering, firstly, data is converted into a graph by using a ε-nearest neighbor method, a k-nearest neighbor (k-NN) method, a complete linkage method, or the like.

Figure 10:
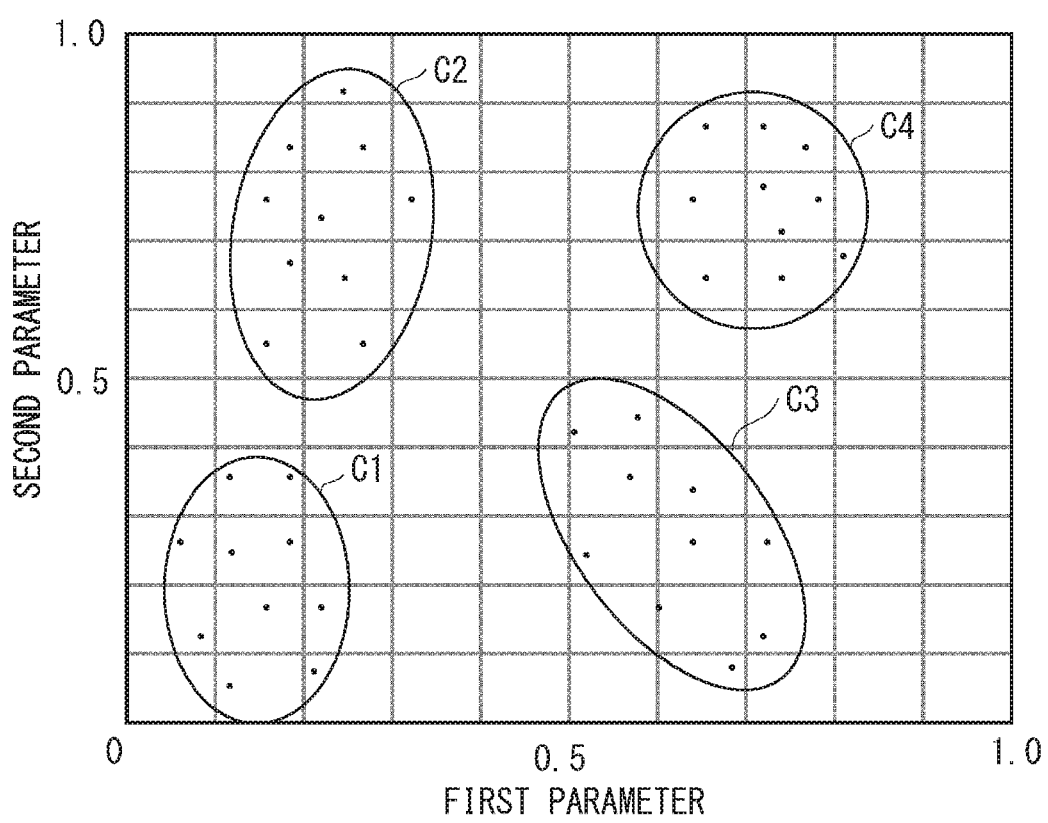
FIG. 10 is a schematic diagram showing an example of a result of a cluster analysis performed in the server shown in FIG. 9.
Figure 11:
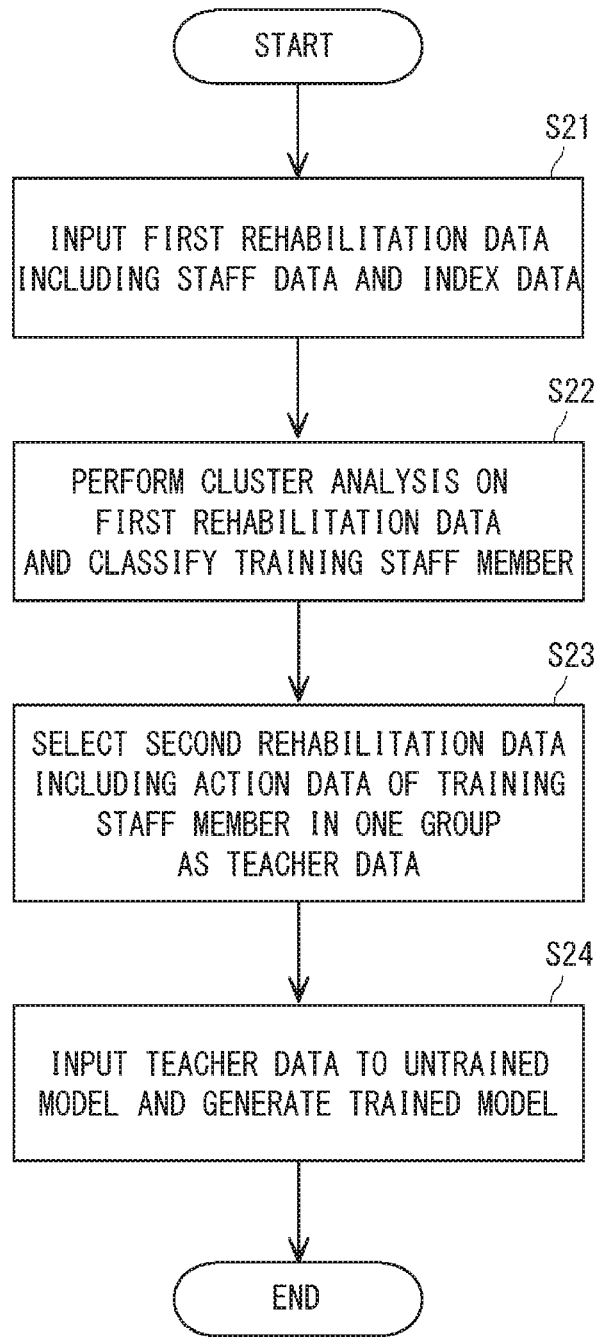
FIG. 11 is a flowchart for explaining an example of learning processes performed in the server shown FIG. 9.

For simplifying the explanation, FIG. 10 shows an example of a result of a cluster analysis performed for two parameters (two items) in the first rehabilitation data. In the example shown FIG. 10, a cluster analysis is performed on the first rehabilitation data while specifying the number of clusters (data groups) as four. As a result, the first rehabilitation data is classified into clusters C1 to C4. Note that, in general, the number of parameters of the cluster analysis (the number of spatial axes) can be made equal to the number of items in the first rehabilitation data. Therefore, the number of parameters can be set to three or larger in this embodiment.

The learning unit 511b generates a trained model that inputs second rehabilitation data including at least action data and outputs action data for suggesting the next action to be performed by the training staff member. In particular, the learning unit 511b selects, as teacher data, second rehabilitation data corresponding to a training staff member included in one of the groups (one of the clusters) into which the training staff members are classified by the analysis unit 511a (step S23). Note that the learning unit 511b may use, as the teacher data, second rehabilitation data corresponding to a training staff member(s) included in only one group. The selection of the teacher data will be described later.

Then, the learning unit 511b inputs the selected teacher data to an untrained model and thereby generates a trained model (step S24). Note that the definition of each data and its example in this embodiment are basically the same as those described in the first embodiment. However, the data selected as the teacher data may be generated from the difference between the level determination unit 510a and the analysis unit 511a.

Further, the learning unit 511b can use, as the teacher data, second rehabilitation data corresponding to a training staff member(s) included in each of a plurality of groups into which into which the training staff members are classified by the analysis unit 511a (i.e., each of a plurality of groups in the classification result). That is, the learning unit 511b may be configured so as to generate a trained model by using, as the teacher data, second rehabilitation data for each of the aforementioned plurality of groups. In this way, a plurality of types of trained models can be generated. In this case, the learning unit 511b may automatically select the teacher data in a predetermined order or the like. In this case, a coordinator (i.e., a user who makes an adjustment) or an operator of the learning model selects a trained model suitable for the use and operates (i.e., makes use of) the selected trained model. For example, it is possible to select a trained model that provides a good correct-answer rate in terms of walking stability, FIM efficiency, walking speed, physical ability, etc. of the trainee as one suitable for the specifications.

Further, the teacher data may also be selected by a coordinator who adjusts the learning model. The coordinator may select, for example, a group that includes a known competent training staff member(s). Therefore, the server 501 may include a group designation unit that designates the aforementioned group (the cluster). Note that the group designation unit may be configured so as to receive designation of a cluster from an external terminal or the like. Then, the learning unit 511b generates a trained model by using, as the teacher data, second rehabilitation data corresponding to a training staff member included in the group designated by the group designation unit. In this way, a trained model that has been trained by using only the designated group can be generated.

Further, the above-described example has been described on the assumption that the analysis unit 511a is provided in the learning apparatus. However, the analysis unit 511a may not be provided in the learning apparatus. In this case, the learning apparatus exemplified by the server 501 may include an acquisition unit that acquires a classification result that is obtained by classifying training staff members by performing a cluster analysis for the first rehabilitation data. This acquisition unit can be formed by, for example, the communication IF 514 and an acquisition control unit in the control unit (e.g., in the response processing unit 511c) that controls the communication IF 511. For example, the acquisition unit may be configured so as to acquire a classification result from an analysis unit provided in an external apparatus such as a PC or the walking training apparatus 100. Alternatively, for example, a person may perform a cluster analysis by using cluster analysis application software based on the first rehabilitation data in a PC or the like. In this case, the acquisition unit may be configured so as to input the result of the cluster analysis (the classification result, e.g., classified staff data) as input data.

Further, the above explanation has been given on the assumption that the learning unit 511b generates a learning model by using, as the teacher data, second rehabilitation data corresponding to a training staff member included in one group in the classification result. In this way, it is possible to generate a trained model in which an action(s) performed by a training staff member(s) belonging to the one group is taken into consideration.

On the other hand, as alternative processing, the learning unit 511b can generate a learning model by using, as the teacher data, second rehabilitation data in which each of a plurality of groups labeled based on the classification result is associated with staff data corresponding to a respective one of the aforementioned plurality of groups. The aforementioned process for the association corresponds to the pre-processing. The aforementioned plurality of groups may be some of all the groups into which the training staff members are classified, or may be all the groups. By using such teacher data, it is possible to generate a trained model in which actions performed by training staff members are taken into consideration on a group-by-group basis.

In other words, in the alternative processing, firstly, each of the groups into which the training staff members are classified is labeled. Next, the learning unit 511$b$ learns action data included in the second rehabilitation data while associating them with the labelled groups by using the second rehabilitation data (excluding the staff data) and the staff data, i.e., by using the second rehabilitation data including the staff data. For example, the association of the learning is performed by labeling the groups so that each group has a different weight. The labeling may be performed in such a manner that, for example, weighting is changed depending on which group staff data of an arbitrary number of training staff members having different degrees of competence belong to. In particular, the labeling may be performed in such a manner that the more competent the training staff members included in the group are, the higher weight that group is assigned.

As described above, as exemplified by the process using one group or the alternative processing, the learning unit 511$b$ generates a learning model by using, as teacher data, second rehabilitation data for which pre-processing has been performed based on a classification result. Note that the aforementioned pre-processing is not limited to the above-described process using one group and the associating processing on a group-by-group basis. For example, in the pre-processing, a classification result may be simply associated with second rehabilitation data. In any case, it is possible to generate, when a trainee performs rehabilitation by using the walking training apparatus 100, a learning model capable of suggesting a desirable action to a training staff member who assists the trainee.

(Operational Stage)

Next, processes preformed in the operation stage in the walking training apparatus 100 and the server 501 will be described. As described above, the walking training apparatus 100 is configured so as to be able to access a trained model, so that it can use the trained model. In the operation stage, in general, the walking training apparatus 100 and the server 501 connected thereto cooperate with each other. That is, they serve as a rehabilitation support system and perform a rehabilitation support process.

The walking training apparatus 100 according to this embodiment can include the output unit and the notification unit described above in the first embodiment in order to operate (i.e., make use of) the above-described trained model. Needless to say, the output unit in this embodiment outputs the second rehabilitation data to the trained model generated in this embodiment.

On the server 501 side, the response processing unit 511$c$ operates the trained model stored in the model storage unit 521 and thereby performs a response process. Further, the server 501 include an input/output unit that inputs the second rehabilitation data output from the above-described output unit to the trained model and outputs an output from the trained model to the walking training apparatus 100. This input/output unit may be exemplified by the communication IF 514 or the like. The aforementioned processes are basically the same as those described above with reference to FIG. 6. Further, examples of their notifications are also the same as those shown in FIGS. 7 and 8.

Through the above-described processes, in the walking training apparatus 100, it is possible to use acquired data as an input parameter, output action data indicating an assisting action to be suggested (an assisting action that was performed by a competent training staff member), and thereby suggest the assisting action to the training staff member. That is, in the walking training apparatus 100, through such a suggestion, it becomes possible to advise the training staff member on an assisting action (setting, assistance, etc.) that he/she should perform next.

Further, the walking training apparatus 100 may also include a designation unit that designates a training staff member who assists the trainee in the above-described rehabilitation. The designation unit is the same as that described in the first embodiment. Further, the walking training apparatus 100 can access a classification result storage unit that stores a result of an analysis (a classification result) by the analysis unit 511$a$. The classification result storage unit may be, for example, a storage device disposed in the overall control unit 210 or connected to the overall control unit 210. Alternatively, the classification result storage unit may be a storage device disposed in the server 501.

Further, in the walking training apparatus 100, when the training staff member designated by the designation unit is a training staff member whose teacher data has not been adopted when the trained model is generated, the output unit outputs second rehabilitation data and the notification unit provides a notification. Therefore, for example, the analysis unit 511$a$ may be configured so as to output, as a part of the analysis result, a name or an ID of the training staff member who took part in (the generation of) the first rehabilitation data that is used as the teacher data. In this way, it is possible to prevent unnecessary notifications from being provided to training staff members who are assumed to require no notification.

Note that the above-described outputting and notification processes are not limited to the processes using one group and may also be applied to the above-described alternative processing. That is, when the group to which the training staff member 901 designated by the designation unit belongs is the group that is used as the teacher data in the trained model, the walking training apparatus 100 may perform the outputting and notification processes.

(Effect)

As described above, this embodiment provides the same effects as those in the first embodiment. That is, in the walking training apparatus 100, it becomes possible to advise the training staff member on an assisting action (setting, assistance, etc.) that he/she should perform next.

(Supplemental Remarks on Method and Program)

As can be understood from the above-described description, in this embodiment, a learning method including the following acquisition step and learning step can also be provided. In the acquisition step, a classification result that is obtained by classifying training staff members by performing a cluster analysis for first rehabilitation data is acquired. The first rehabilitation data includes at least staff data for the rehabilitation performed by the trainee by using the walking training apparatus 100, action data indicating an assisting action performed by the training staff member to assist the trainee, and index data indicating the degree of recovery of the trainee. In the learning step, a learning model that inputs second rehabilitation data including at least action data and outputs action data for suggesting the next action to be performed by the training staff member is generated. Further, in the learning step, a learning model is generated by using, as teacher data, second rehabilitation data for which pre-processing has been performed based on the classification result.

In this embodiment, as can be understood from the above-described description, it is also possible to provide a method for supporting rehabilitation (a method for operating the walking training apparatus 100) in the walking training apparatus 100 capable of accessing a trained model, which is a learning model trained by the above-described learning method. The method includes the outputting step and the notification step described in the first embodiment.

In this embodiment, as can be understood from the above-described description, it is also possible to provide a program (a learning program) for causing a computer to perform the above-described analysis step and the learning step. Needless to say, it is also possible to provide a trained model trained by the learning apparatus, a trained model trained by the learning method, and a trained model trained by the learning program. Further, in this embodiment, as can be understood from the above-described description, it is also possible to provide a rehabilitation support program for causing a computer of the walking training apparatus 100 capable of accessing the above-described trained model to perform the above-described outputting step and notification step.

Fourth Embodiment

In the third embodiment, an example in which the server 501 includes the analysis unit 511a and the learning unit 511b, and the server 501 generates a trained model is shown. In contrast, in this embodiment, the analysis unit and the learning unit are provided on the walking training apparatus 100 side (e.g., in the overall control unit 210). A rehabilitation support system according to this embodiment may include the walking training apparatus 100. However, in this case, in order to increase the amount of rehabilitation data collected in the learning stage, the rehabilitation support system may be configured so that rehabilitation data from other walking training apparatuses can be collected.

Further, regarding the operation stage, an example in which the trained model is provided in the server 501, and the walking training apparatus 100 transmits rehabilitation data to the server 501 and receives action data from the server 500 has been described. However, the present disclosure is not limited to such examples. For example, a trained model may be incorporated on the walking training apparatus 100 side (e.g., in a storage unit in the overall control unit 210). For this purpose, the walking training apparatus 100 may include a storage unit that stores the trained model. Further, although it is not specifically described, the various examples described above in the first and third embodiments can also be applied to this embodiment. For example, in this embodiment, an acquisition unit may also be provided in place of the analysis unit as in the third embodiment. That is, the walking training apparatus 100 according to this embodiment may include an acquisition unit in place of the analysis unit.

Fifth Embodiment

The first to fourth embodiments have been described on the assumption that a notification is provided to a person such as the training staff member 901. However, a notification can also be provided to a non-human training assistant (e.g., a mechanical or artificial training assistant). As the artificial training assistant, there are various types of assistants such as a humanoid robot, a voice assistant program, and a display assistant program. As an example in which a voice assistant program assists the trainee by voice, it is possible to give encouraging talks such as "Please lean your upper body further to the right", "Please hold the handrails", and "Please slow down your walking speed".

When the training assistant is a computer program, it can be incorporated in the walking training apparatus 100 in an executable manner. Alternatively, the program may also be incorporated, in an executable manner, in a portable terminal such as a mobile phone (including a smartphone), a mobile PC, or an external server capable of communicating with the walking training apparatus 100. Further, the artificial training assistant may also include a program with artificial intelligence (an AI program).

Further, a plurality of artificial training assistants may be made available when walking training is performed in the walking training apparatus 100, and each of them may be separately managed in a distinguishable manner. That is, even when the training assistant is an artificial training assistant, the training assistant can be distinguished from other training assistants as in the case of the human training staff member.

Further, when an artificial training assistant is used, examples of the data (the assistant data) related to the artificial training assistant corresponding to the data related to the training staff member 901 in the above-described item (4) include the below-shown data. The examples include functions (such as a voice assist function and an assistance function using a video display) of the artificial training assistant (the program), and a name and a version of the program. Further, when the program is a type of an AI program that learns during its operation, the examples include a learning algorithm, a degree of learning, a learning time, and the number of times of learning.

Further, in the case where a plurality of training assistants (irrespective of whether the assistant is a human assistant or a non-human assistant) simultaneously assist the rehabilitation, the rehabilitation data may include assistant data of the plurality of assistants as in the case of the plurality of human training staff members as described above. Further, each assistant data may also include information indicating whether the assistant is a main training assistant or an assistance training assistant. In addition to or instead of the aforementioned information, each assistant data may include information indicating what kind of assistance is provided.

A notification in this embodiment will be described. For example, when a notification to an artificial training assistant, rather than the human assistant such as the training staff member 901, is required, the notification control unit 210d may notify the artificial training assistant. The notification may be directly provided through communication. Alternatively, the notification may be provided by a video image or a voice as in the case of the human assistant and the video or voice notification may be detected by the artificial training assistant. Further, the artificial training assistant may be configured so as to be able to change the setting or the like of the walking training apparatus 100 through communication or a direct-touching operation. In this way, even the artificial training assistant can perform an action that is suggested during the operation of the trained model.

ALTERNATIVE EXAMPLE

Each of the above-described embodiments is described by using an example in which the trainee 900 is a hemiplegic patient who has a disorder in one of his/her legs. However, the walking training apparatus 100 can also be applied to a patient whose legs are both paralyzed. In this case, the patient does training with walking assistance apparatuses 120 attached to both legs. In this case, abnormal walking may be evaluated for each of the diseased legs. The degree of recovery can be individually determined for each diseased leg by independently evaluating abnormal walking for each leg.

Further, although it is not shown in the drawings, the walking training apparatus may be an apparatus that is not equipped with the treadmill 131 of the walking training apparatus 100 shown in FIG. 1, so that the trainee 900 can actually move in the space surrounded by the frame 130. In this case, the frame 130 may be formed so that it has a large length in the traveling direction. Further, it may adopt a configuration in which the harness pulling unit 112, the front pulling unit 135, and the rear pulling unit 137 are moved along guide rails by a motor(s) (not shown) as the trainee 900 moves. Since the trainee 900 actually moves relative to the floor surface, he/she can feel a sense of accomplishment of rehabilitation training more effectively. Needless to say, the walking training apparatus is not limited to these configuration examples.

Further, as described above, a rehabilitation support apparatus according to each embodiment may be an apparatus for supporting other kinds of rehabilitation, i.e., rehabilitation other than the walking training, or for supporting training other than the rehabilitation. In such a case, a learning apparatus according to each embodiment can be a learning apparatus that generates a trained model that is adapted to that apparatus, and uses input parameters and output parameters corresponding to the type of the rehabilitation or the type of the training. Examples of the training other than the rehabilitation include exercises such as walking and running and training. Further, a training support apparatus corresponding to the type of the training can be used. Further, the index data in the case of the training other than the rehabilitation may be data indicating the degree of an improvement in a physical function of the trainee instead of the degree of recovery of the trainee. The degree of an improvement in a physical function may include an improvement in a muscle strength by an exercise or the like and/or an improvement in endurance. Further, even when the training is the rehabilitation, the index data may be data indicating the degree of an improvement in a physical function of the trainee. In this case, the degree of an improvement in a physical function may include the degree of recovery by the rehabilitation or the like. Further, in the case of the training other than the rehabilitation, the first rehabilitation data and the second rehabilitation data can be referred to as first training data and second training data, respectively, or simply as first data and second data, respectively.

Further, a rehabilitation support apparatus described in each embodiment may be formed as a rehabilitation support system by using a plurality of apparatuses. Similarly, the walking training apparatus may be formed as a walking training system by using a plurality of apparatuses, and the training support apparatus may be formed as a training support system by using a plurality of apparatuses. Further, for example, a server (a server apparatus) described in each embodiment may not be equipped with the learning apparatus but may be equipped only with the trained model. Further, the server may be equipped with all of or only some of the functions of the learning apparatus. Further, a server apparatus described in each embodiment may include at least some of the functions and parts described as the functions and parts of the rehabilitation support apparatus. Further, the above-described rehabilitation support apparatus or the server apparatus may have a hardware configuration including, for example, a processor, a memory, and a communication interface. These apparatuses are implemented by making the processor load and execute a program stored in the memory.

Such a program, i.e., a learning program and a trained model described in each embodiment are described hereinafter.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer through a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A learning system comprising:
an acquisition unit configured to acquire a classification result obtained by classifying training assistants by performing a cluster analysis for first rehabilitation data about rehabilitation performed by a trainee by using a rehabilitation support system, the first rehabilitation data including at least assistant data indicating a training assistant who assists the trainee, action data indicating an assisting action performed by the training assistant to assist the trainee, and index data indicating a degree of recovery of the trainee; and
a learning unit configured to generate a learning model, the learning model being configured to input second rehabilitation data including at least the action data and output the action data for suggesting a next action to be performed by the training assistant, wherein
the learning unit generates the learning model by using, as teacher data, the second rehabilitation data for which pre-processing has been performed based on the classification result.

2. The learning system according to claim 1, wherein the second rehabilitation data includes at least one of the index data and the assistant data.

3. The learning system according to claim 1, wherein the learning unit generates the learning model by using, as the teacher data, the second rehabilitation data corresponding to the training assistant included in one group in the classification result.

4. The learning system according to claim 1, wherein the learning unit generates the learning model by using the second rehabilitation data as the teacher data, the second rehabilitation data being data in which a plurality of groups that are labeled based on the classification result are associated with the assistant data each of which corresponds to a respective one of the plurality of groups.

5. The learning system according to claim 1, further comprising an analysis unit configured to classify the training assistants by performing the cluster analysis for the first rehabilitation data, wherein
the acquisition unit acquires a classification result obtained by classifying the training assistants from the analysis unit.

6. The learning system according to claim 1, wherein the first and second rehabilitation data includes trainee data indicating a feature of the trainee.

7. The learning system according to claim 6, wherein the trainee data includes symptom data indicating at least one of a disease and a symptom of the trainee.

8. The learning system according to claim 1, wherein the action data includes at least one of data indicating an operation by which a setting value in the rehabilitation support system has been changed and data indicating an assisting action for the trainee.

9. The learning system according to claim 8, wherein the data indicating the operation includes data indicating a level of skill required for performing the operation.

10. The learning system according to claim 1, wherein the learning unit generates the learning model for each of a plurality of groups in the classification result by using, as the teacher data, the second rehabilitation data corresponding to the training assistant included in that group.

11. The learning system according to claim 1, further comprising a group designation unit configured to designate one group in the classification result, wherein
the learning unit generates the learning model by using, as the teacher data, the second rehabilitation data corresponding to the training assistant included in the group designated by the group designation unit.

12. A rehabilitation support system capable of accessing a trained model, the trained model being a learning model trained by the learning system according to claim 1, the rehabilitation support system comprising:
an output unit configured to output the second rehabilitation data about rehabilitation performed by a trainee by using the rehabilitation support system as an input to the trained model, and
a notification unit configured to notify the training assistant assisting the trainee in the rehabilitation of the action data output from the trained model.

13. The learning system according to claim 12, further comprising a designation unit configured to designate the training assistant who assists the trainee in the rehabilitation, wherein
the rehabilitation support system is accessible to a classification result storage unit configured to store the classification result, and
when the training assistant designated by the designation unit is a training assistant whose teacher data has not been adopted when the trained model is generated, the output unit outputs the second rehabilitation data and the notification unit provides a notification.

14. A non-transitory computer readable medium storing a trained model, the trained model being a learning model that has been trained by the learning system according to claim 1.

15. A learning system comprising:
an acquisition unit configured to acquire a classification result obtained by classifying training assistants by performing a cluster analysis for first data about training performed by a trainee by using a training support system, the first data including at least assistant data indicating a training assistant who assists the trainee, action data indicating an assisting action performed by the training assistant to assist the trainee, and index data indicating a degree of an improvement in a physical function of the trainee; and
a learning unit configured to generate a learning model, the learning model being configured to input second data including at least the action data and output the action data for suggesting a next action to be performed by the training assistant, wherein
the learning unit generates the learning model by using, as teacher data, the second data for which pre-processing has been performed based on the classification result.

16. A learning method comprising:
an acquisition step of acquiring a classification result obtained by classifying training assistants by performing a cluster analysis for first rehabilitation data about rehabilitation performed by a trainee by using a rehabilitation support system, the first rehabilitation data including at least assistant data indicating a training assistant who assists the trainee, action data indicating an assisting action performed by the training assistant to assist the trainee, and index data indicating a degree of recovery of the trainee; and
a learning step of generating a learning model, the learning model being configured to input second rehabilitation data including at least the action data and output the action data for suggesting a next action to be performed by the training assistant, wherein
in the learning step, the learning model is generated by using, as teacher data, the second rehabilitation data for which pre-processing has been performed based on the classification result.

17. A rehabilitation support method in a rehabilitation support system capable of accessing a trained model, the trained model being a learning model trained by the learning method according to claim 16, the rehabilitation support method comprising:
an outputting step of outputting, by the rehabilitation support system, the second rehabilitation data about rehabilitation performed by a trainee by using the rehabilitation support system as an input to the trained model, and
a notification step of notifying, by the rehabilitation support system, the training assistant assisting the trainee in the rehabilitation of the action data output from the trained model.

18. A non-transitory computer readable medium storing a program for causing a computer to perform:
an acquisition step of acquiring a classification result obtained by classifying training assistants by performing a cluster analysis for first rehabilitation data about rehabilitation performed by a trainee by using a rehabilitation support system, the first rehabilitation data including at least assistant data indicating a training assistant who assists the trainee, action data indicating an assisting action performed by the training assistant to assist the trainee, and index data indicating a degree of recovery of the trainee; and
a learning step of generating a learning model, the learning model being configured to input second rehabilitation data including at least the action data and output the action data for suggesting a next action to be performed by the training assistant, wherein
in the learning step, the learning model is generated by using, as teacher data, the second rehabilitation data for which pre-processing has been performed based on the classification result.

19. A non-transitory computer readable medium storing a rehabilitation support program for a computer of a rehabilitation support system, the rehabilitation support system being capable of accessing a trained model, the trained model being a learning model trained by the program stored in the non-transitory computer readable medium according to claim 18, the rehabilitation support program being configured to cause the computer to perform:
- an outputting step of outputting the second rehabilitation data about rehabilitation performed by a trainee by using the rehabilitation support system as an input to the trained model, and
- a notification step of notifying the training assistant assisting the trainee in the rehabilitation of the action data output from the trained model.

20. A non-transitory computer readable medium storing a trained model, the trained model being a learning model that has been trained by the program stored in the non-transitory computer readable medium according to claim 18.

* * * * *